(12) United States Patent
Tachibana et al.

(10) Patent No.: US 10,626,360 B2
(45) Date of Patent: *Apr. 21, 2020

(54) NUCLEIC ACID AMPLIFICATION DEVICE

(71) Applicant: PANASONIC INTELLECTUAL PROPERTY MANAGEMENT CO., LTD., Osaka (JP)

(72) Inventors: Hiroaki Tachibana, Osaka (JP); Shogo Shibuya, Osaka (JP)

(73) Assignee: PANASONIC CORPORATION, Osaka (JP)

( * ) Notice: Subject to any disclaimer, the term of this patent is extended or adjusted under 35 U.S.C. 154(b) by 17 days.

This patent is subject to a terminal disclaimer.

(21) Appl. No.: 15/325,227

(22) PCT Filed: Jul. 30, 2015

(86) PCT No.: PCT/JP2015/003836
§ 371 (c)(1),
(2) Date: Jan. 10, 2017

(87) PCT Pub. No.: WO2016/021158
PCT Pub. Date: Feb. 11, 2016

(65) Prior Publication Data
US 2017/0175067 A1    Jun. 22, 2017

(30) Foreign Application Priority Data
Aug. 8, 2014    (JP) .................................. 2014-162209

(51) Int. Cl.
*C12M 3/06* (2006.01)
*B01L 3/00* (2006.01)
(Continued)

(52) U.S. Cl.
CPC ........... *C12M 23/16* (2013.01); *B01L 3/5027* (2013.01); *B01L 3/502746* (2013.01); *B01L 7/52* (2013.01);
(Continued)

(58) Field of Classification Search
CPC ..... C12M 23/16; C12M 21/18; B01L 3/5027; B01L 3/502746
See application file for complete search history.

(56) References Cited

U.S. PATENT DOCUMENTS 5,726,026 A * 3/1998 Wilding et al. .... B01D 67/0062
366/DIG. 3
8,222,049 B2 * 7/2012 Linder et al. ..... B01L 3/502746
435/174

(Continued)

FOREIGN PATENT DOCUMENTS

CN    101535466    9/2009
JP    2002-18271    1/2002
(Continued)

OTHER PUBLICATIONS

Tachibana et al., "Capillary Ryoku Kudo no Jisoshiki Microflow PCR Device no Kaihatsu to Byogentai JinsokuKenshutsu eno Oyo", 94th Annual Meeting of the Chemical Society of Japan in Spring Koen Yokoshu, Mar. 12, 2014, pp. 3G2-51.
(Continued)

*Primary Examiner* — Gautam Prakash
(74) *Attorney, Agent, or Firm* — Greenblum & Bernstein, P.L.C.

(57) ABSTRACT

A nucleic acid amplification device which includes a flow channel for feeding a reaction solution containing a target nucleic acid includes: a nucleic acid amplification reaction portion that amplifies the target nucleic acid contained in the reaction solution; and a fed-solution retention portion that
(Continued)

retains the reaction solution. The flow channel includes a first flow channel disposed in the nucleic acid amplification reaction portion and a second flow channel disposed in the fed-solution retention portion, and the reaction solution fed from the first flow channel is retained in the second flow channel.

12 Claims, 20 Drawing Sheets

(51) Int. Cl.
*C12M 1/40* (2006.01)
*C12M 1/00* (2006.01)
*C12M 1/34* (2006.01)
*B01L 7/00* (2006.01)
*C12N 15/09* (2006.01)
*C12Q 1/68* (2018.01)

(52) U.S. Cl.
CPC ............. *C12M 1/00* (2013.01); *C12M 1/34* (2013.01); *C12M 21/18* (2013.01); *B01L 2300/0816* (2013.01); *B01L 2300/0883* (2013.01); *B01L 2400/0406* (2013.01); *C12N 15/09* (2013.01); *C12Q 1/68* (2013.01)

(56) References Cited

U.S. PATENT DOCUMENTS

| | | | |
|---|---|---|---|
| 8,231,845 B2* | 7/2012 | Wyzgol et al. | B01L 3/502746 422/412 |
| 8,414,847 B2* | 4/2013 | Davis | F04B 19/006 422/502 |
| 2006/0228258 A1* | 10/2006 | Sannsoondar | G01N 21/03 422/82.05 |
| 2009/0162929 A1* | 6/2009 | Ikeda | B01L 7/525 435/303.1 |
| 2009/0311713 A1 | 12/2009 | Pollack et al. | |
| 2011/0253222 A1 | 10/2011 | Arai | |
| 2012/0115738 A1 | 5/2012 | Zhou et al. | |
| 2014/0220668 A1 | 8/2014 | Tachibana et al. | |
| 2015/0031087 A1 | 1/2015 | Nagai et al. | |
| 2015/0190811 A1 | 7/2015 | Tachibana et al. | |
| 2016/0199840 A1 | 7/2016 | Tachibana et al. | |

FOREIGN PATENT DOCUMENTS

| | | |
|---|---|---|
| JP | 2005-130795 | 5/2005 |
| JP | 2005-147840 | 6/2005 |
| JP | 2008-82961 | 4/2008 |
| JP | WO2010/061598 | 6/2010 |
| JP | 2011-501665 | 1/2011 |
| JP | 2011-520449 | 7/2011 |
| JP | 2011-200193 | 10/2011 |
| JP | 4993260 | 5/2012 |
| WO | 2008/011486 | 1/2008 |
| WO | 2008/044387 | 4/2008 |
| WO | 2009/022496 | 2/2009 |
| WO | 2013/027393 | 2/2013 |
| WO | 2013/132645 | 9/2013 |
| WO | 2013/190745 | 12/2013 |
| WO | 2015/019626 | 2/2015 |

OTHER PUBLICATIONS

Search Report issued in International Bureau of WIPO Patent Application No. PCT/JP2015/003836, dated Nov. 2, 2015.
Hiroaki Tachibana et al., "On-chip Quantitative detection of pathogen genes by autonomous microfluidic PCR platform", Biosensors and Bioelectronics, vol. 74, XP055392101 , Jul. 9, 2015, pp. 725-730.
Search Report issued in European Patent Office (EPO) Patent Application No. 15830003.8, dated Aug. 3, 2017.
Office Action issued in China Counterpart Patent Appl. No. 201580039002.4, dated Jun. 11, 2018 , along with a partial english translation thereof.

* cited by examiner

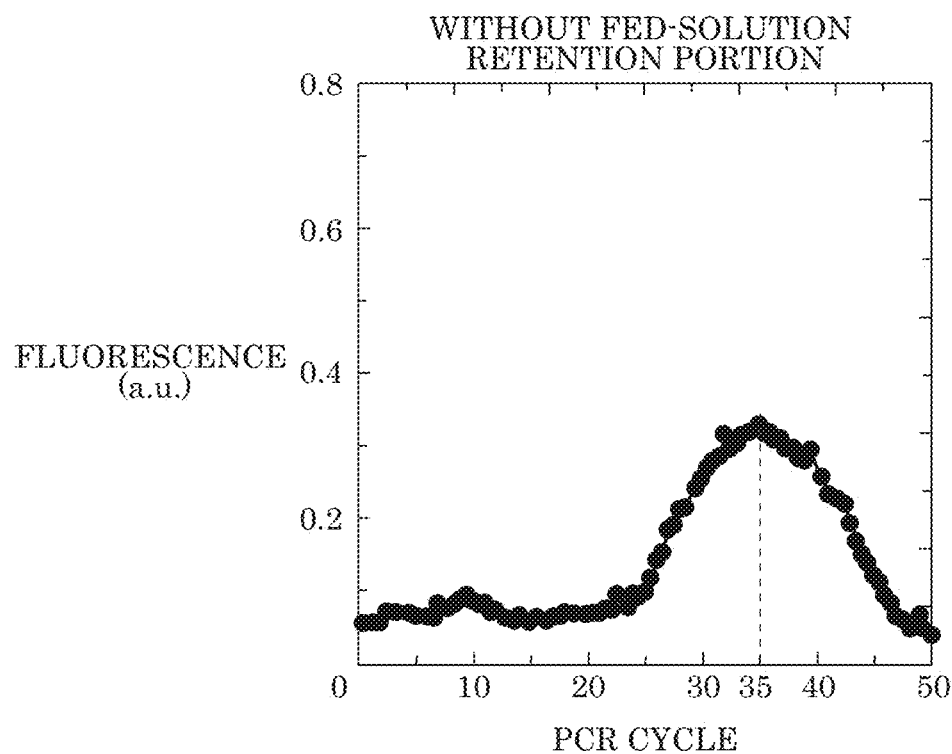
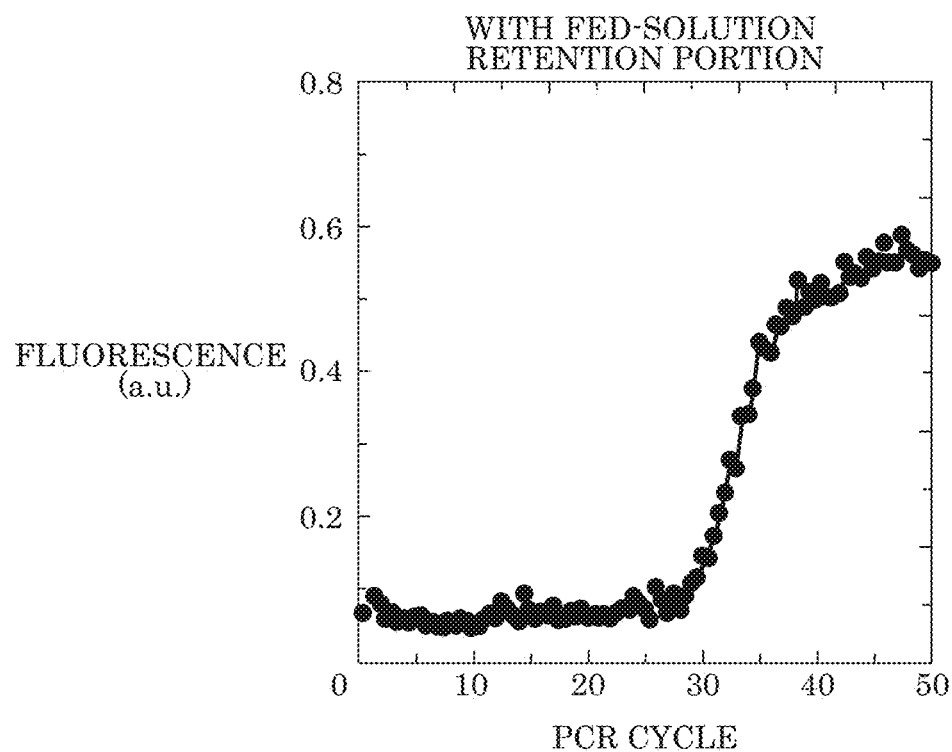

(i) REGION IN WHICH FLUID FRONT OF SOLUTION IS LOCATED IN NUCLEIC ACID AMPLIFICATION REACTION PORTION
(ii) REGION IN WHICH FLUID FRONT OF SOLUTION IS LOCATED IN FED-SOLUTION RETENTION PORTION

E.COLI GENOME DNA CONCENTRATION

- ● 1.9 pg/μl
- △ 0.19 pg/μl
- ■ 0.019 pg/μl
- ◇ 0.0019 pg/μl
- ○ NC

NUCLEIC ACID AMPLIFICATION DEVICE

TECHNICAL FIELD

The present invention relates to a nucleic acid amplification device.

BACKGROUND ART

A nucleic acid amplification device is used for amplifying a sample of a target nucleic acid. For example, the nucleic acid amplification device amplifies the target nucleic acid by repeatedly subjecting a reaction solution (a reaction fluid) that contains the target nucleic to desired temperature changes.

Moreover, using a microfluidic device is known as a method of rapidly making the temperature changes for the reaction solution. The microfluidic device allows the reaction solution containing an extremely small amount of sample and reagent to react. Examples of such a microfluidic device include a microreaction device (microreactor), an integrated deoxyribonucleic acid (DNA) device, and a microelectrophoresis device.

For example, Patent Literatures (PTLs) 1 and 2 disclose dividing a device into a plurality of different temperature zones and providing a channel that is serpentine (a serpentine channel) to allow a reaction solution to repeatedly flows through the temperature zones. With this structure, the speed of the temperature changes made to the reaction solution can be enhanced. Thus, when a solution containing a nucleic acid is used as the reaction solution, the nucleic acid can be amplified rapidly.

CITATION LIST

Patent Literatures

PTL 1: Japanese Unexamined Patent Application Publication No. 2002-18271
PTL 2: Japanese Patent No. 4993260

SUMMARY OF THE INVENTION

Problem that Invention is to Solve

However, it is difficult for a conventional nucleic acid amplification device to amplify a target nucleic acid contained in a reaction solution with high accuracy.

The present invention was conceived to solve the aforementioned problem, and has an object to provide a nucleic acid amplification device that is capable of amplifying a reaction solution with high accuracy.

Means to Solve Problem

To achieve the aforementioned object, a nucleic acid amplification device according to an aspect of the present invention is a nucleic acid amplification device which includes a flow channel for feeding a reaction solution containing a target nucleic acid, the nucleic acid amplification device comprising: a nucleic acid amplification reaction portion that amplifies the target nucleic acid contained in the reaction solution; and a fed-solution retention portion that retains the reaction solution, wherein the flow channel includes a first flow channel disposed in the nucleic acid amplification reaction portion and a second flow channel disposed in the fed-solution retention portion, and the reaction solution fed from the first flow channel is retained in the second flow channel.

Advantageous Effect of Invention

With the present invention, a target nucleic acid contained in a reaction solution can be amplified with high accuracy.

BRIEF DESCRIPTION OF DRAWINGS

FIG. 6A is a diagram showing a relationship between a polymerase chain reaction (PCR) cycle of a reaction solution and the amount of fluorescence (the amount of amplification) when nucleic acid amplification is performed using a nucleic acid amplification device according to a comparative example.
FIG. 6B is a diagram showing a relationship between a PCR cycle of a reaction solution and the amount of fluorescence (the amount of amplification) when nucleic acid amplification is performed using a nucleic acid amplification device according to an embodiment.

DESCRIPTION OF EXEMPLARY EMBODIMENTS

Figure 1A:
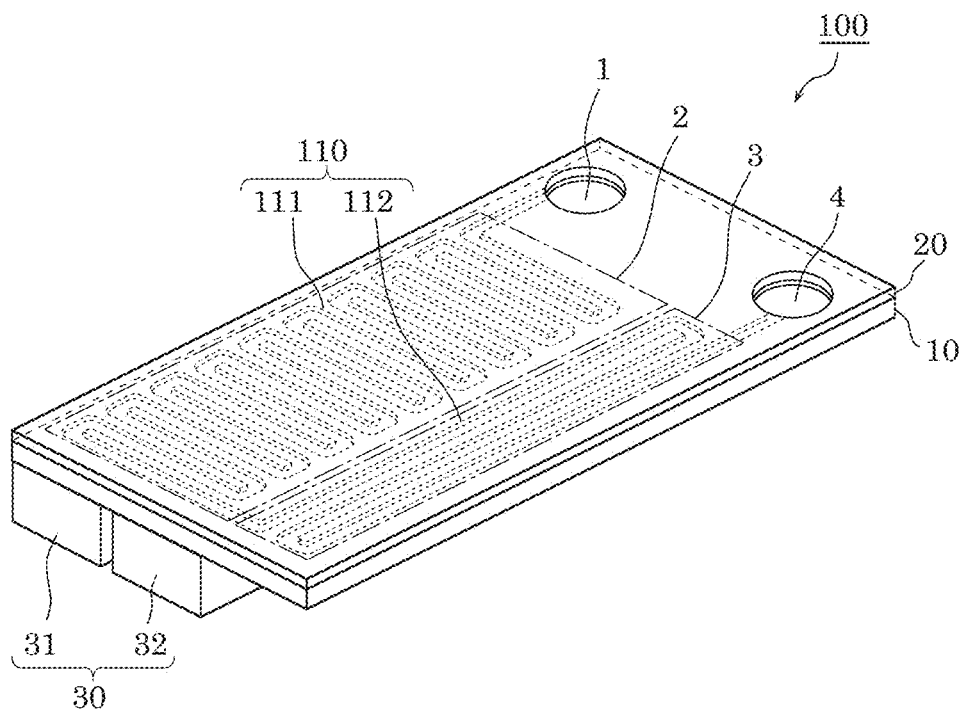
FIG. 1A is a perspective view of a nucleic acid amplification device according to an embodiment.

The following describes embodiments according to the present invention, with reference to the drawings. It should be noted that each of the embodiments described below represents only a preferred specific example. The numerical values, shapes, materials, structural components, the arrangement and connection of the structural components, steps, the processing order of the steps, and so forth shown in the following embodiments are mere examples, and are not intended to limit the scope of the present invention. Furthermore, among the structural components in the following embodiments, components not recited in any one of the independent claims which indicate the broadest concepts of the present invention are described as arbitrary structural components.

It should be noted that each of the drawings is a schematic diagram and is not necessarily a precise illustration. Note also that, in all the drawings, the same reference numerals are given to the substantially same structural components and redundant description thereof shall be omitted or simplified.

(Embodiment)

Figure 1B:
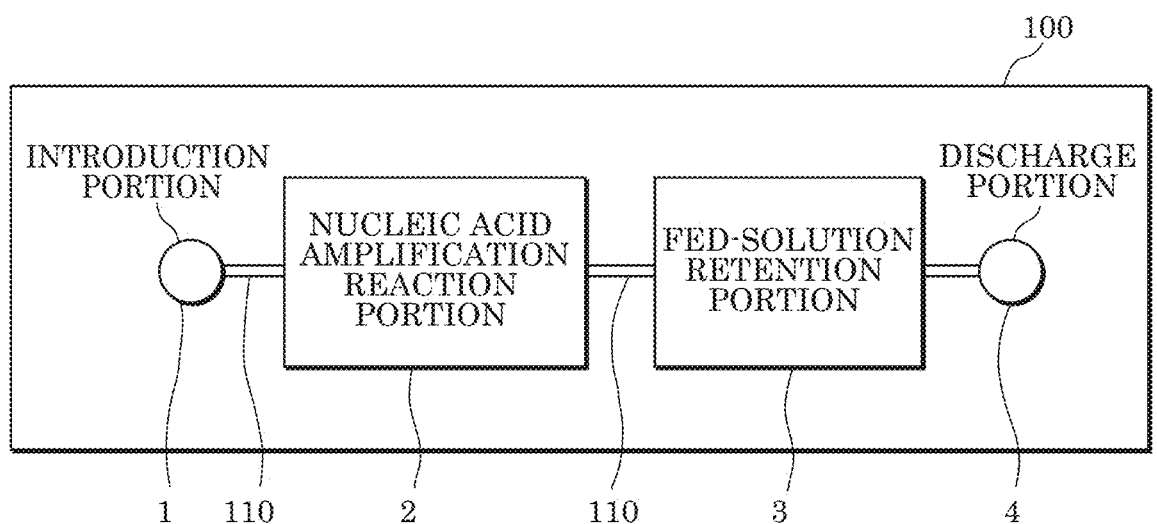
FIG. 1B is a diagram showing a schematic configuration of a nucleic acid amplification device according to an embodiment.
Figure 2:
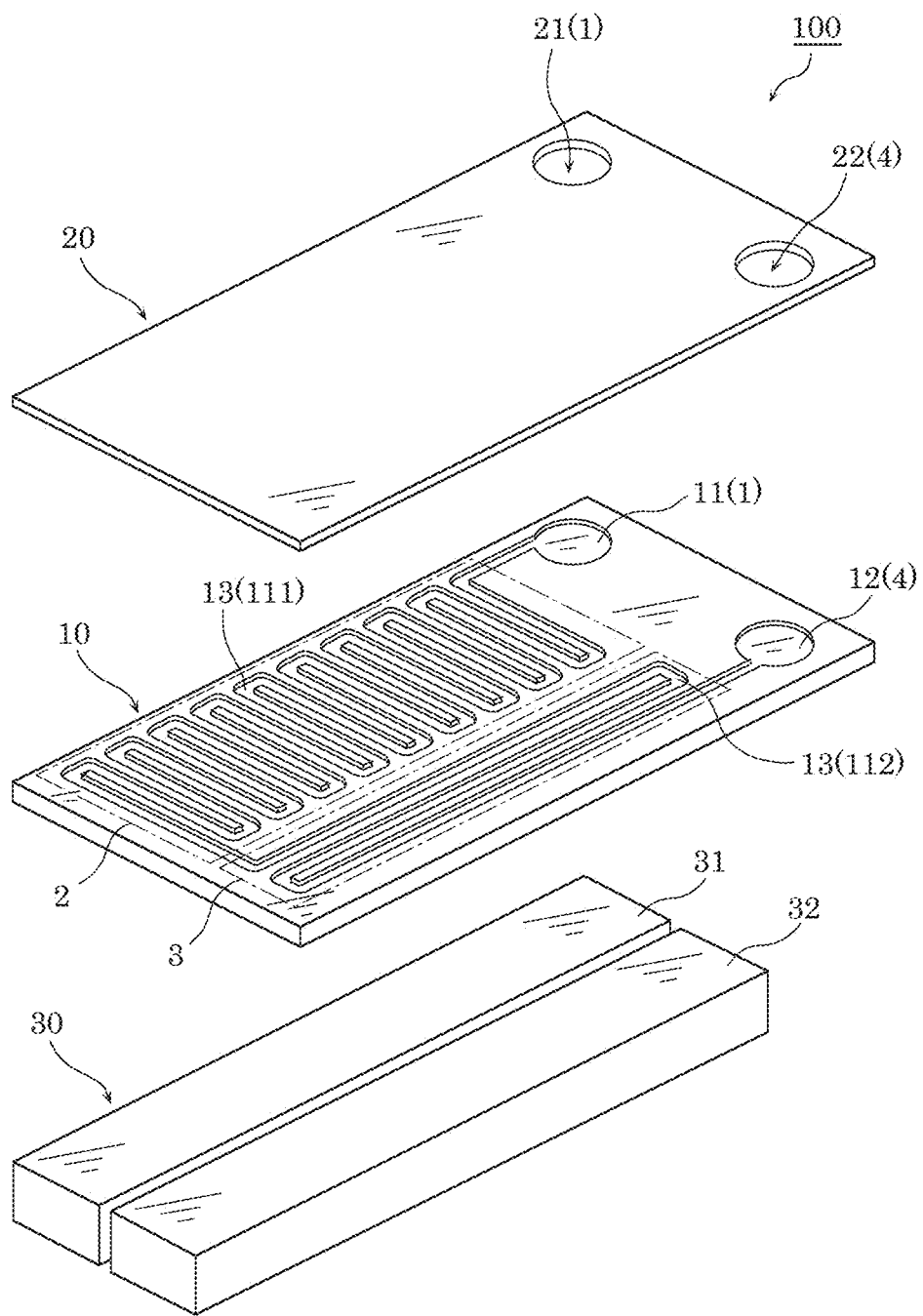
FIG. 2 is an exploded perspective view of a nucleic acid amplification device according to an embodiment.
Figure 3:
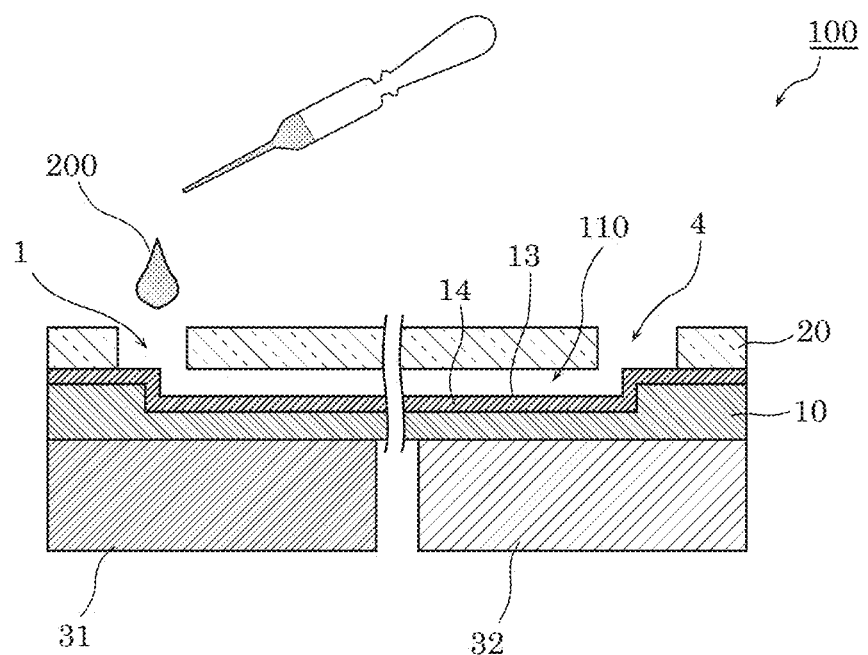
FIG. 3 is a cross-sectional view of a nucleic acid amplification device according to an embodiment.

A configuration of nucleic acid amplification device 100 according to an embodiment of the present invention is described, with reference to FIG. 1A, FIG. 1B, FIG. 2, and FIG. 3. FIG. 1A is a perspective view of the nucleic acid amplification device according to the embodiment. FIG. 1B is a diagram showing a schematic configuration of the nucleic acid amplification device. FIG. 2 is an exploded perspective view of the nucleic acid amplification device. FIG. 3 is a cross-sectional view of the nucleic acid amplification device.

As shown in FIG. 1A to FIG. 3, nucleic acid amplification device 100 is a device (a device chip) that amplifies a sample of a target nucleic acid. Nucleic acid amplification device 100 includes introduction portion 1, nucleic acid amplification reaction portion 2, fed-solution retention portion 3, and discharge portion 4.

Introduction portion 1 is a sample introduction opening (inlet) into which a reaction solution containing the sample of the target nucleic acid is introduced.

Nucleic acid amplification reaction portion 2 is a nucleic acid amplification reaction region for amplifying the target nucleic acid contained in the reaction solution that is introduced into introduction portion 1.

Fed-solution retention portion 3 is a fed-solution retention region for retaining the reaction solution. To be more specific, fed-solution retention portion 3 is a fed-solution advancement portion for advancing the fluid front part of the reaction solution beyond nucleic acid amplification reaction portion 2 without retaining the fluid front in nucleic acid amplification reaction portion 2. Fed-solution retention portion 3 is capable of retaining a given amount of the reaction solution. It should be noted that the reaction solution that is retained in fed-solution retention portion 3 may be stationary or flowing continuously.

Discharge portion 4 is a sample discharge opening (drain) from which the reaction solution containing the target nucleic acid amplified in nucleic acid amplification reaction portion 2 is discharged. Note that the reaction solution may not be discharged from discharge portion 4.

Moreover, nucleic acid amplification device 100 includes flow channel 110 for feeding the reaction solution containing the target nucleic acid. Flow channel 110 is a reaction flow channel through which the reaction solution flows in only one direction. Furthermore, flow channel 110 is configured to pass through at least nucleic acid amplification reaction portion (nucleic acid amplification reaction region) 2 and fed-solution retention portion (fed-solution retention region) 3. In the present embodiment, flow channel 110 is configured with a single channel that has one end part connected to introduction portion 1 and the other end part connected to discharge portion 4.

Flow channel 110 includes first flow channel 111 disposed in nucleic acid amplification reaction portion 2 and second flow channel 112 disposed in fed-solution retention portion 3. Second flow channel 112 is a flow channel for retaining the reaction solution in fed-solution retention portion 3. Moreover, second flow channel 112 is configured to retain a predetermined amount of the reaction solution including the fluid front part of the reaction solution fed to fed-solution retention portion 3 (second flow channel 112). Since fed-solution retention portion 3 is disposed downstream of nucleic acid amplification reaction portion 2, the reaction solution fed from first flow channel 111 (nucleic acid amplification reaction portion 2) is retained in second flow channel 112.

A volumetric capacity (cubic volume) of second flow channel 112 is 10% or more of a total volumetric capacity (cubic volume) of flow channel 110, or preferably 30% or more of the total volumetric capacity (cubic volume) of flow channel 110. In the present embodiment, the volumetric capacity of second flow channel 112 is about 30% of the total volumetric capacity of flow channel 110.

In the present embodiment, the reaction solution introduced into flow channel 110 via introduction portion 1 is fed through flow channel 110 by capillary force. For example, by making an inner surface of flow channel 110 a hydrophilic surface having an acute contact angle, the reaction solution can be fed by capillary force.

The reaction solution (reaction fluid) is a solution containing at least a sample of a target nucleic acid. In the present embodiment, the reaction solution is an aqueous solution containing a target nucleic acid and a reaction reagent for amplifying the target nucleic acid. It should be noted that the reaction solution may contain a certain type of alcohol or a surfactant, for example.

This embodiment describes a case of performing a polymerase chain reaction (PCR) method using nucleic acid amplification device 100.

The PCR method is a technique of amplifying target DNA according to thermal cycling. The reaction solution contains, for example, a PCR primer, a polymerase enzyme, and a buffer, in addition to the target DNA. By subjecting this reaction solution to the thermal cycling, the target DNA can be amplified. The amount of the amplified DNA can be detected using a reaction detection system.

Furthermore, nucleic acid amplification device 100 according to the present embodiment is a microfluidic device having flow channel 110 as a micro flow channel. To be more specific, nucleic acid amplification device 100 is configured with first substrate 10, second substrate 20, and heater 30.

Heater 30 includes first heater block 31 and second heater block 32 that have different set temperatures. Here, for example, nucleic acid amplification device 100 has the outer shape that is roughly rectangular and is 40 mm long and 20 mm wide.

Hereinafter, configurations of the structural components included in nucleic acid amplification device 100 are described in detail, with reference to FIG. 1A to FIG. 3.

[First Substrate]

As shown in FIG. 2, first substrate 10 includes the following: first recessed portion 11 that forms a part of introduction portion 1; second recessed portion 12 that forms a part of discharge portion 4; and groove portion 13 that forms flow channel 110. First substrate 10 is a silicon substrate, for example.

Groove portion 13 (flow channel 110) is formed so as to connect first recessed portion 11 and second recessed portion 12. The reaction solution flows through groove portion 13 (flow channel 110). To be more specific, when the reaction solution is introduced into first recessed portion 11 (introduction portion 1), this reaction solution advances through groove portion 13 (flow channel 110) toward second recessed portion 12 (discharge portion 4).

As shown in FIG. 2, flow channel 110 (first flow channel 111) in nucleic acid amplification reaction portion 2 is a serpentine flow channel formed to be serpentine to alternately pass through first heater block 31 (first temperature zone) and second heater block 32 (second temperature zone) repeatedly.

To be more specific, first flow channel 111 is formed in such a manner that a linear flow channel is bended repetitively back on itself (back and forth) at predetermined intervals. The number of bendings of first flow channel 111 is about 20 to 70 cycles, for example. However, the number of bendings is not limited to this example. As an example, the length of first flow channel 111 per cycle may be 32 mm.

Moreover, flow channel 110 (second flow channel 112) in fed-solution retention portion 3 according to the present embodiment includes a serpentine portion (serpentine flow channel). To be more specific, second flow channel 112 is formed in such a manner that a linear flow channel is bended repetitively back on itself (back and forth) at predetermined intervals. The number of bendings and flowing direction of second flow channel 112 may be set as appropriate according to space availability. Note that second flow channel 112 according to the present embodiment is disposed so as not to be located above heater 30.

As shown in FIG. 3, silicon oxide film 14 is formed on the inner surface of groove portion 13 forming flow channel 110. Forming silicon oxide film 14 allows the wall surface (inner surface) of flow channel 110 (groove portion 13) to be hydrophilic.

Flow channel 110 configured in this way is a micro flow channel and has, for example, a rectangular cross-sectional shape. In this case, the flow channel width (groove width) of groove portion 13 forming flow channel 110 is about 20 μm to 300 μm, for example, and the depth of groove portion 13 is about 50 μm to 150 μm.

It should be noted that the cross-sectional shape of groove portion 13 is not limited to a rectangle, and may be a semicircle or an inverted triangle. Moreover, first recessed portion 11 and second recessed portion 12 may be recessed portions having circular openings, for example. First substrate 10 may be either one of a translucent substrate, such as a transparent substrate, and an opaque substrate. Moreover, first substrate 10 is not limited to a silicon substrate, and may be a resin substrate or a glass substrate, for example.

[Second Substrate]

As shown in FIG. 1A, second substrate 20 is a lid portion that covers first substrate 10 and thus is disposed on first substrate 10. Second substrate is a transparent silicon substrate or a glass substrate, for example.

As shown in FIG. 2, second substrate 20 includes, as a part of introduction portion 1, first through hole 21 that penetrates second substrate 20. Second substrate 20 further includes, as a part of discharge portion 4, second through hole 22 that penetrates second substrate 20. Each of first through hole 21 and second through hole 22 is a through hole having, for example, a circular opening.

As shown in FIG. 3, since second substrate 20 is disposed on first substrate 10, the opening portion of groove portion 13 is covered up and thus flow channel 110 is formed to be sealed in all directions. With this, all the wall surfaces of flow channel 110 are enclosed in a cross section taken perpendicular to the feeding direction (travelling direction) of the reaction solution. Thus, flow channel 110 is connected to an external space only in introduction portion 1 and discharge portion 4. With flow channel 110 enclosed in all the directions in this way, capillary force in flow channel 110 can be enhanced and the reaction solution can be inhibited from volatilizing while being fed.

It should be noted that the material used for second substrate 20 is not limited to resin and glass and may be silicon, for example.

[Heater]

Heater 30 is a heating device for heating the reaction solution containing the target nucleic acid. As shown in FIG. 1A to FIG. 2, heater 30 is disposed opposite to at least nucleic acid amplification reaction portion 2. The reaction solution fed through flow channel 110 (first flow channel 111) in nucleic acid amplification reaction portion 2 is subjected to a predetermined temperature by heater 30.

In the present embodiment, nucleic acid amplification reaction portion 2 is provided with, as heater 30, first heater block 31 and second heater block 32 that are set at predetermined different temperatures. In other words, the two heater blocks, i.e., first heater block 31 and second heater block 32, form two temperature zones set at the predetermined different temperatures in nucleic acid amplification reaction portion 2.

Note that first heater block 31 and second heater block 32 are heaters formed using, for example, cuboid metal blocks comprising a metal such as aluminum or stainless steel. Other than such a heater block, a metal thin film heater that is formed by, for example, printing a metal thin film on a glass substrate may be used for instance as heater 30.

A region in which first heater block 31 set at a first temperature is disposed is a first temperature zone. Moreover, a region in which second heater block 32 set at a second temperature is disposed is a second temperature zone that is different from the first temperature zone.

In the present embodiment, the temperature of first heater block 31 is set higher than the temperature of second heater block 32. More specifically, the region in which first heater block 31 is disposed is a high temperature zone, and the region in which second heater block 32 is disposed is a low temperature zone.

The temperature of first heater block 31, which is the high temperature zone, is 93° C. to 98° C., for example. In the present embodiment, the temperature of first heater block 31 is set at about 95° C., which is the temperature at which denaturation of the nucleic acid amplification reaction occurs. On the other hand, the temperature of second heater block 32, which is the low temperature zone, is 50° C. to 75° C., for example. In the present embodiment, the temperature of second heater block 32 is set at about 60° C., which is the temperature at which annealing and extension of the reaction occur.

Heater 30 is connected to a temperature controller (not illustrated). With this temperature controller, each of the temperatures of first heater block 31 and second heater block 32 can be controlled.

First heater block 31 and second heater block 32 are arranged with a predetermined space from each other. First substrate 10 is disposed on first heater block 31 and second heater block 32. To be more specific, first substrate 10 is placed on heater 30 so that first flow channel 111 runs across first heater block 31 and second heater block 32. With this, first flow channel 111 is formed to pass back and forth through the two temperature zones in a plurality of cycles.

It should be noted that, in the present embodiment, fed-solution retention portion 3 (second flow channel 112) is not disposed opposite to heater and thus is not directly subjected to a temperature of heater 30.

[Nucleic Acid Amplification Method]

Figure 4:
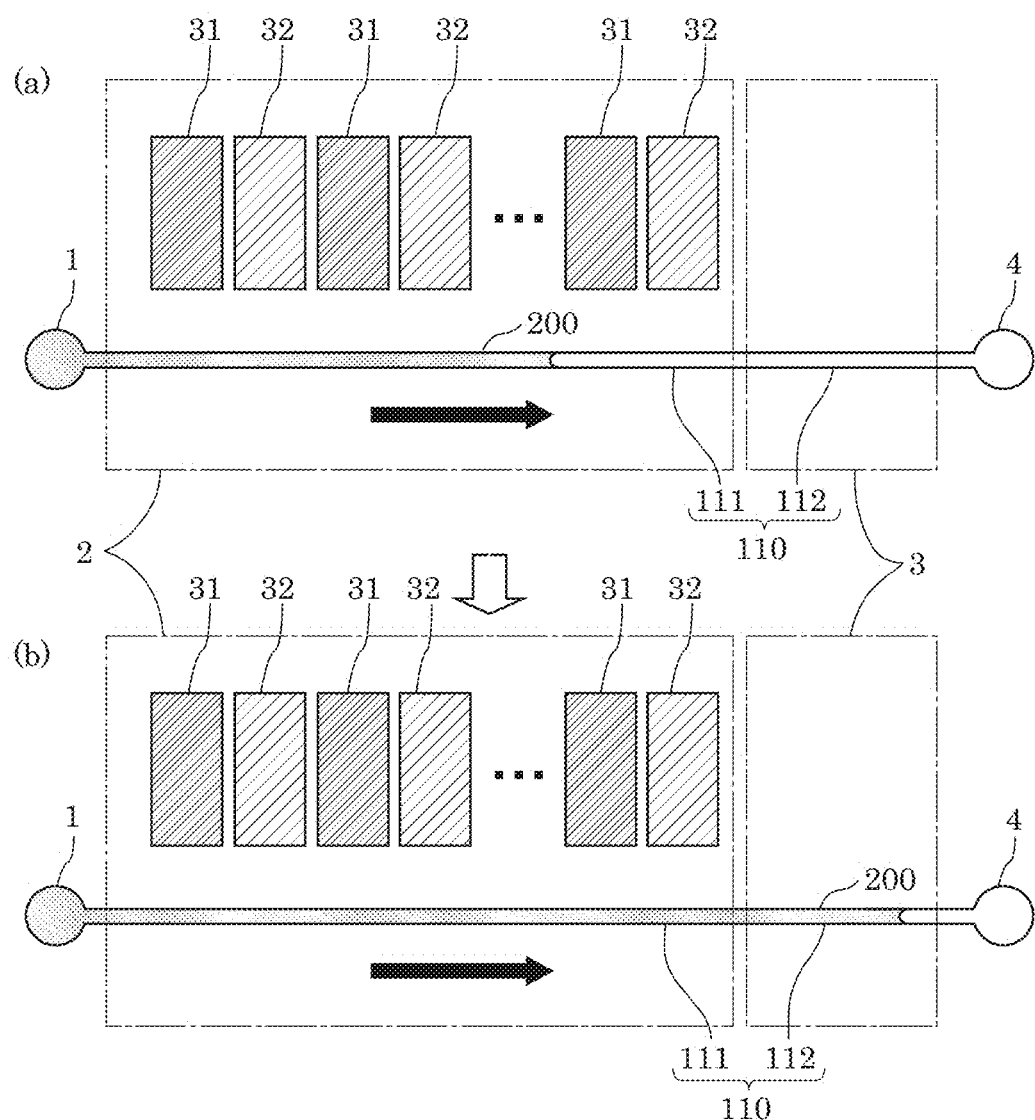
FIG. 4 is an explanatory diagram showing a thermal cycle of a nucleic acid amplification device according to an embodiment.

Next, the nucleic acid amplification method performed using nucleic acid amplification device 100 is described, using FIG. 4 with reference to FIG. 1A to FIG. 3. FIG. 4 is an explanatory diagram showing a thermal cycle of the nucleic acid amplification device according to the embodiment. In this figure, (a) shows that the fluid front of the reaction solution passes through the nucleic acid amplification reaction portion and (b) shows that the fluid front of the reaction solution passes through the fed-solution retention portion.

Firstly, a sample of a target nucleic acid and a reaction reagent for amplifying the target nucleic acid are introduced into introduction portion 1 of nucleic acid amplification device 100. To be more specific, the reaction solution containing the target nucleic acid and the reaction reagent are previously mixed, and then this premixed solution is introduced as reaction solution 200 into introduction portion 1 of nucleic acid amplification device 100. For example, reaction solution 200 is dispensed into introduction portion 1 with a pipette, as shown in FIG. 3.

As shown in FIG. 1B and (a) of FIG. 4, reaction solution 200 introduced into introduction portion 1 is fed from introduction portion 1 to nucleic acid amplification reaction portion 2 through flow channel 110.

In nucleic acid amplification reaction portion 2, the target nucleic acid contained in reaction solution 200 is amplified when reaction solution 200 is subjected to cyclic temperature changes.

To be more specific, reaction solution 200 reaching nucleic acid amplification reaction portion 2 passes through flow channel 110 (first flow channel 111), repeatedly traveling back and forth between first heater block 31 and second heater block 32, as shown in (a) of FIG. 4. In other words, reaction solution 200 is fed so as to sequentially pass alternately and repeatedly between the two temperature zones, which are the high temperature zone (first heater block 31) and the low temperature zone (second heater block 32) of nucleic acid amplification reaction portion 2. This means that reaction solution 200 is alternately and repeatedly heated and cooled. With this, reaction solution 200 flowing through flow channel 110 (first flow channel 111) can be subjected to a heat cycle. As a result, the target nucleic acid contained in reaction solution 200 is amplified by the repetitions of denaturation reaction in the high temperature zone and annealing-extension reaction in the low temperature zone.

Since the temperature of reaction solution 200 can be increased and decreased as reaction solution 200 is fed in this way, extremely rapid flow PCR can be achieved. Hence, the target nucleic acid contained in reaction solution 200 can be amplified rapidly.

After this, reaction solution 200 is fed to discharge portion 4 by fed-solution retention portion 3 as shown in FIG. 1B and (b) of FIG. 4. This means that a fixed portion from the fluid front (tip) of reaction solution 200 is retained in fed-solution retention portion 3. More specifically, a portion of reaction solution 200 having a fixed length measured in a downstream direction from the portion present in discharge portion 4 (the fluid front part) is retained in fed-solution retention portion 3.

In the present embodiment, when the fluid front of reaction solution 200 introduced in introduction portion 1 reaches discharge portion 4, introduction of the solution containing the target nucleic acid (that is the reaction solution in the present embodiment) into introduction portion 1 is stopped. At this time, flow channel 110 is completely filled with reaction solution 200.

In the present embodiment, reaction solution 200 is fed through flow channel 110 by capillary force as advancing through flow channel 110, as described above. (from 0022) For example, by making the inner surface of flow channel 110 (first flow channel 111 and second flow channel 112) a hydrophilic surface having an acute contact angle, reaction solution 200 can be fed by capillary force. In the present embodiment, the inner surface of groove portion 13 is made hydrophilic by forming silicon oxide film 14 on three walls of groove portion 13 of flow channel 110, that is, a bottom portion and both side walls of groove portion 13. In this way, the inner wall surface of flow channel 110 is made a hydrophilic surface in the present embodiment.

With this, since self-propelled flow of reaction solution 200 is achieved in flow channel 110 by capillary force caused at the air-liquid interface, reaction solution 200 automatically advances through flow channel 110.

Thus, in nucleic acid amplification reaction portion 2, the target nucleic acid contained in reaction solution 200 is amplified as reaction solution 200 is fed by capillary force through flow channel 110 (first flow channel 111). In other words, the target nucleic acid is amplified as reaction solution 200 is subjected to the cyclic temperature changes in nucleic acid amplification reaction portion 2 as reaction solution 200 is fed through flow channel 110 by automatic transport.

Although part of the wall surface of flow channel 110 may be hydrophilic, it is more preferable that the entire wall surface of flow channel 110 in a cross section taken perpendicular to the solution feeding direction is hydrophilic. In this case, not only the surface of groove portion 13 of first substrate 10, but also the surface (inner surface) of second substrate 20 may be made hydrophilic. The greater the proportion of the surface that is hydrophilic in the wall surface of flow channel 110 in cross section, the greater the capillary force acting on reaction solution 200.

[Nucleic Acid Amplification Device]

Figure 5:
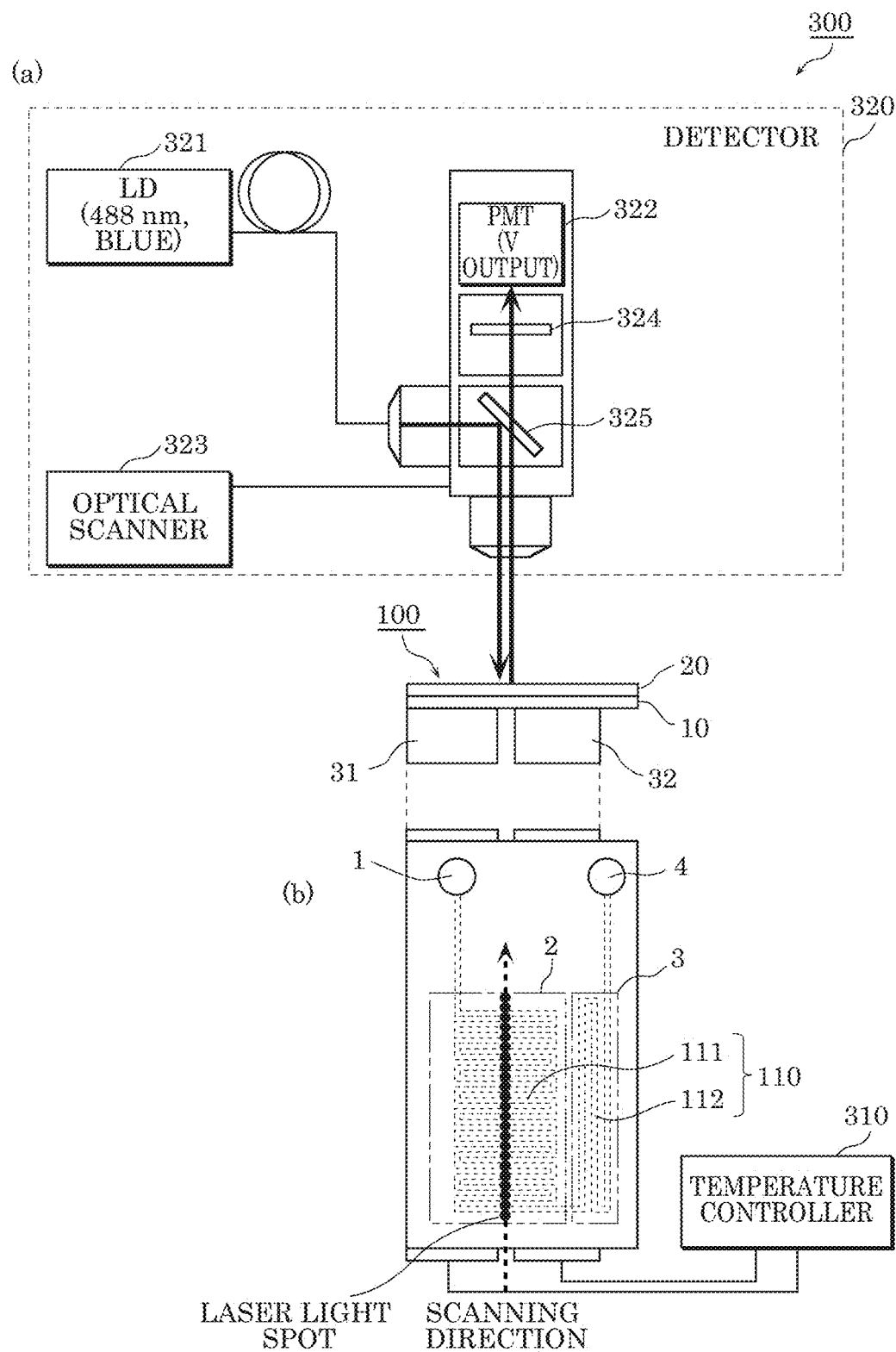
FIG. 5 is a diagram showing a configuration of a nucleic acid amplification device according to an embodiment.

Next, nucleic acid amplification apparatus 300 according to an embodiment is described with reference to FIG. 5. FIG. 5 is a diagram showing a configuration of a nucleic acid amplification apparatus according to an embodiment.

As shown in FIG. 5, nucleic acid amplification device 300 according to the present embodiment includes nucleic acid amplification device 100 described above and temperature controller 310 that controls the temperature of nucleic acid amplification reaction portion 2 of nucleic acid amplification device 100. With this configuration, nucleic acid amplification can be achieved by a simple method.

As shown in (a) of FIG. 5, nucleic acid amplification apparatus 300 according to the present embodiment further includes detector 320 that detects nucleic acid amplification of the target nucleic acid.

Detector 320 is an optical detection system, and includes the following: light output section 321 that outputs light for irradiating nucleic acid amplification device 100; light receptor 322 that receives reflected light of the light irradiating nucleic acid amplification device 100; and optical scanner 323 that scans flow channel 110 of nucleic acid amplification device 100 with light.

Light output section 321 has a laser element that emits blue light, and outputs, for example, laser light with a central wavelength of 488 nm. Light receptor 322 is a photomultiplier tube (PMT), for example. Note that detector 320 further includes other optical elements, such as excitation cut filter 324 and dichroic mirror 325.

In this way, nucleic acid amplification apparatus 300 according to the present embodiment is an integrated evaluation system configured with a heating-cooling system (temperature controller 310) and an optical detection system (detector 320). Such integration with the detection system can achieve a simple detection apparatus. Moreover, such integration with the optical detection system can achieve non-contact detection of the amount of amplification of the nucleic acid.

Here, assume that the amount of amplification of the target nucleic acid contained in the reaction solution (the reaction sample and the reaction reagent) introduced into nucleic acid amplification device 100 is to be detected. In this case, scanning is performed with laser light in a direction intersecting flow channel 110 (first flow channel 111) of nucleic acid amplification reaction portion 2, as shown in (b) of FIG. 5, and then the reflected light is received. Then, on the basis of the received reflected light, the amount of amplification of the target nucleic acid contained in the reaction solution within first flow channel 111 is calculated.

From this, a nucleic acid amplification curve can be obtained that corresponds to the cycle of first flow channel 111 running back and forth between first heater block 31 and second heater block 32. In other words, scanning first flow channel 111 with the laser light allows the amount of amplification of the nucleic acid to be detected for each cycle of first flow channel 111 as an amplification curve. To be more specific, the amplification curve can be obtained that shows that the amount of amplification of the nucleic acid increases with an increase in the number of PCR cycles.

In the present embodiment, irradiation of the reaction solution with blue laser light allows the blue light to act as excitation light, which causes green light emitted by fluorescence to reflect back as reflected light. The amount of fluorescence of this green light (reflected light) varies according to the amount of amplification of the nucleic acid. On this account, the amount of amplification of the nucleic acid can be calculated by measuring the amount of fluorescence of the green light.

[Advantageous Effects and Experimental Examples]

Next, advantageous effects of nucleic acid amplification device 100 according to the present embodiment are described along with the underlying knowledge forming the basis of the present invention and experimental examples, with reference to FIG. 6A and FIG. 6B.

FIG. 6A is a diagram showing a relationship between a PCR cycle of a reaction solution and the amount of fluorescence (the amount of amplification) when nucleic acid amplification is performed using a nucleic acid amplification device according to a comparative example. FIG. 6B is a diagram showing a relationship between a PCR cycle of the reaction solution and the amount of fluorescence (the amount of amplification) when nucleic acid amplification is performed using the nucleic acid amplification device according to the embodiment shown in FIG. 1A.

The nucleic acid amplification device according to the comparative example has a configuration that does not include fed-solution retention portion 3 (second flow channel 112) included in nucleic acid amplification device 100 shown in FIG. 1A. In each of FIG. 6A and FIG. 6B, a reaction solution containing human genome beta-actin (β-atin) as the reaction sample (PCR reagent) was used. Moreover, the amount of amplification of the nucleic acid was calculated based on the amount of fluorescence using the nucleic acid amplification apparatus described above and shown in FIG. 5.

As shown in FIG. 6A, when the nucleic acid amplification device according to the comparative example is used, it can be seen that the amount of fluorescence increases with an increase in the number of PCR cycles (that is, the amount of nucleic acid increases) and that the amount of fluorescence decreases after the number of PCR cycles exceeds a given number of cycles (that is, the amount of nucleic acid decreases). To be more specific, it can be seen that the amount of fluorescence decreases after 35 PCR cycles in the case where the total number of PCR cycles is 50.

This is believed to be because the fluid front part of the reaction solution fed through the flow channel reduces in reaction efficiency due to, for example, absorption of the reaction reagent by the wall surface of the flow channel or a concentration change of the reaction solution as a result of evaporation of the reaction solution.

In this way, as indicated by the nucleic acid amplification device according to the comparative example, it is difficult for a conventional nucleic acid amplification device to amplify the reaction solution with high accuracy.

In view of this, the inventors of the present invention thought that the target nucleic acid in the reaction solution could be amplified with high accuracy by separating the fluid front part with a low reaction efficiency out of the reaction solution from the reaction solution that enables a desired efficiency.

More specifically, as shown in FIG. 1A and FIG. 1B, the inventors conceived an idea of disposing fed-solution retention portion 3 downstream of nucleic acid amplification reaction portion 2 and causing fed-solution retention portion 3 to retain the fluid front part with a low reaction efficiency out of the reaction solution. With this idea, the fluid front part of the reaction solution fed by flow channel 110 can be advanced toward fed-solution retention portion 3 without stagnating in nucleic acid amplification reaction portion 2 and then can be retained in fed-solution retention portion 3.

As a result, the fluid front part with a low reaction efficiency out of the reaction solution can be separated from the reaction solution that enables a desired efficiency. In other words, since the fluid front part with a low reaction efficiency out of the reaction solution is retained in fed-solution retention portion 3, nucleic acid amplification reaction portion 2 can retain the rear portion of the reaction solution having no decrease in reaction efficiency and thus enabling a desired efficiency.

With fed-solution retention portion 3 provided as described, the fluid front part with a low reaction efficiency out of the reaction solution can be withdrawn from nucleic acid amplification reaction portion 2. As a result, a desired amount of fluorescence (signal value) can be obtained even when the number of PCR cycles continues to increase.

In fact, when nucleic acid amplification device 100 including fed-solution retention portion 3 is used, the amount of fluorescence continues to increase, instead of decreasing, with an increase in the number of PCR cycles, as can be seen in FIG. 6B. In other words, it can be seen that the amount of nucleic acid continues to increase with an increase in the number of PCR cycles.

Moreover, as shown in FIG. 6A, when fed-solution retention portion 3 is not provided, the reaction efficiency decreases during the last 15 cycles out of the total PCR cycles (50 cycles) (15/50=30%). Thus, when human genome is used as the target nucleic acid in the reaction solution, the volumetric capacity of second flow channel 112 may be 30% or more of the total volumetric capacity of flow channel 110.

In FIG. 6A, the maximum number of cycles is 50. However, according to the experimental results, it was found that the reaction efficiency decreased at the point 15 cycles back from the fluid front part even when the maximum number of cycles was 60 or 70. This situation is believed to be seen at least until when the maximum number of cycles is 150.

Hence, in order to appropriately withdraw the fluid front part with a low reaction efficiency out of the reaction solution, the volumetric capacity of flow channel 110 (second flow channel 112) in fed-solution retention portion 3 may be at least 10% or more of the total volumetric capacity of flow channel 110. In other words, the cubic volume of the reaction solution retained in fed-solution retention portion 3 (the retained volume) may be 10% or more of the total cubic volume of the reaction solution completely filling flow channel 110. With this, as shown in FIG. 6B, the target nucleic acid can be amplified with high accuracy without a decrease in reaction efficiency.

Figure 7:
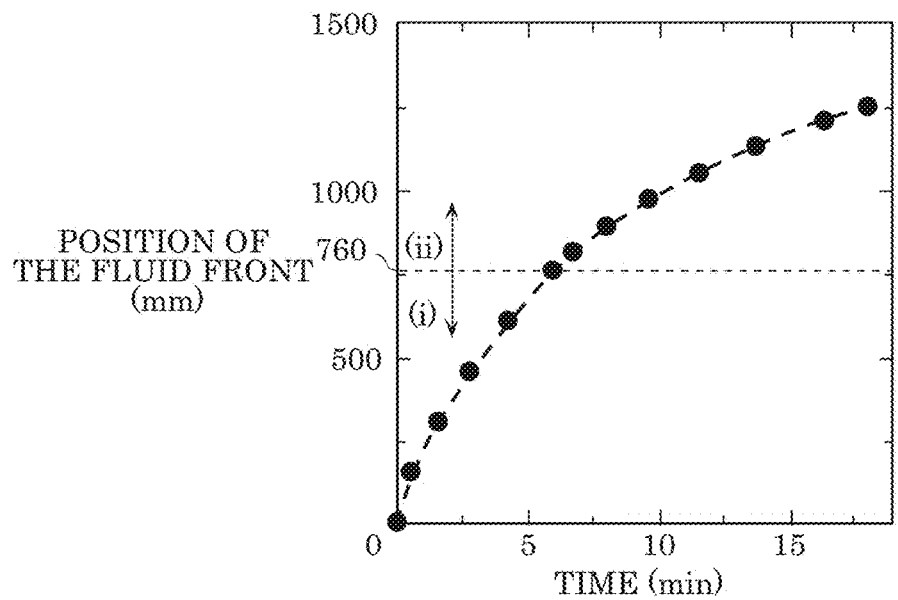
FIG. 7 is a diagram showing a relationship between a solution feeding time and a position of the fluid front when a reaction solution is fed using a nucleic acid amplification device according to an embodiment.

Next, the solution feeding characteristics of nucleic acid amplification device 100 according to the present embodiment are described with reference to FIG. 7. FIG. 7 is a diagram showing a relationship between a solution feeding time and a position of the fluid front when the reaction solution is fed using a nucleic acid amplification device according to an embodiment. Note that the solution feeding time is the time measured from the beginning of the feeding, and that the position of the fluid front is the position of the front (fluid front) of the reaction solution in the flow channel. Moreover, a solution containing β-actin Detection Reagents (manufactured by Life Technologies Corporation) and human genome DNA was used as the reaction sample.

As shown in FIG. 7, the fluid front of the reaction solution is located in nucleic acid amplification reaction portion 2, in the region from 0 mm to 760 mm (region (i)). Moreover, as shown in FIG. 7, the fluid front of the reaction solution is located in fed-solution retention portion 3, in the region from 760 mm to 1260 mm (region (ii)).

Furthermore, it can be seen that the reaction solution fills nucleic acid amplification reaction portion 2 in 6 minutes and subsequently fills fed-solution retention portion 3 in 12 minutes.

As a result, the average feeding velocity in fed-solution retention portion 3 was about 0.68 mm/s. In the present embodiment, such feeding control over the subsequent reaction solution with fed-solution retention portion 3 was able to achieve an efficient nucleic acid amplification reaction.

(Experimental Results)

The following describes experimental results to evaluate amplification characteristics of nucleic acid amplification device 100 according to the present embodiment.

(Example 1)

Firstly, Example 1 that is an example to detect human genome DNA is described with reference to FIG. 8, FIG. 9, and FIG. 10.

Figure 8:
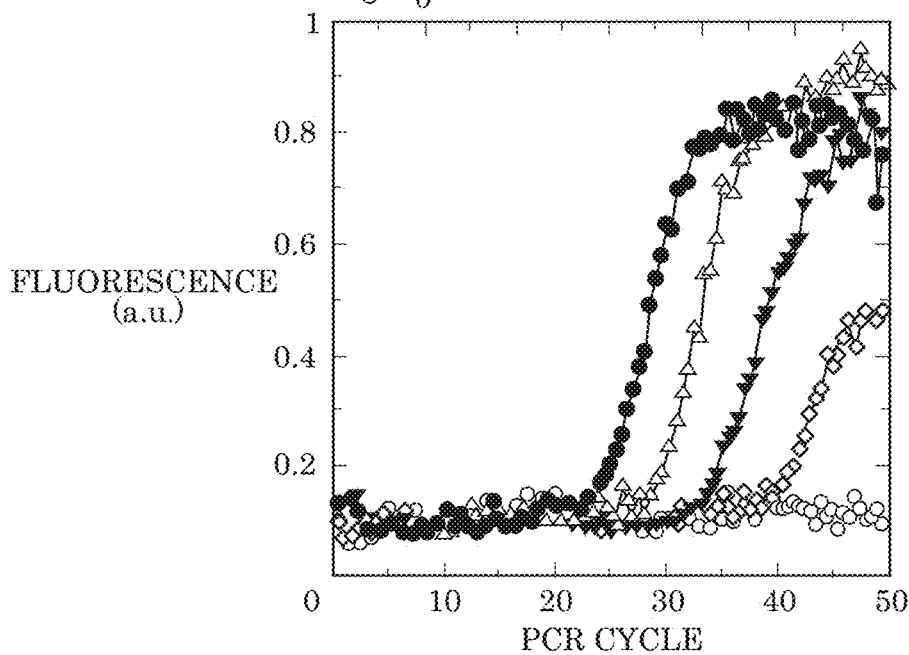
FIG. 8 is a diagram showing a relationship between a PCR cycle of a reaction solution and the amount of fluorescence (the amount of amplification) when human genome DNA is amplified using a nucleic acid amplification device according to an embodiment.

FIG. 8 is a diagram showing a relationship between a PCR cycle of the reaction solution and the amount of fluorescence (the amount of amplification) when the human genome DNA is amplified using the nucleic acid amplification device according to the embodiment. In FIG. 8, measurement results of optical detection performed using the nucleic acid amplification apparatus shown in FIG. 5 are shown.

In this experiment, a solution containing β-actin Detection Reagents (manufactured by Life Technologies Corporation) and human genome DNA was used as the reaction sample (PCR sample).

Moreover, amplification characteristics were evaluated for each of the cases in which the respective final concentrations of the human genome DNA were 3200 pg/μl, 400 pg/μl, 40 pg/μl, and 4 pg/μl. Furthermore, as a negative control (NC), amplification characteristics were also evaluated for the solution that did not contain human genome DNA (0 pg/μl as the concentration of human genome DNA).

As can be seen in FIG. 8, the amount of fluorescence increased with an increase in the number of PCR cycles in all the cases of the human genome DNA concentrations. In other words, it can be seen that the amount of nucleic acid increased in all the cases.

Figure 9:
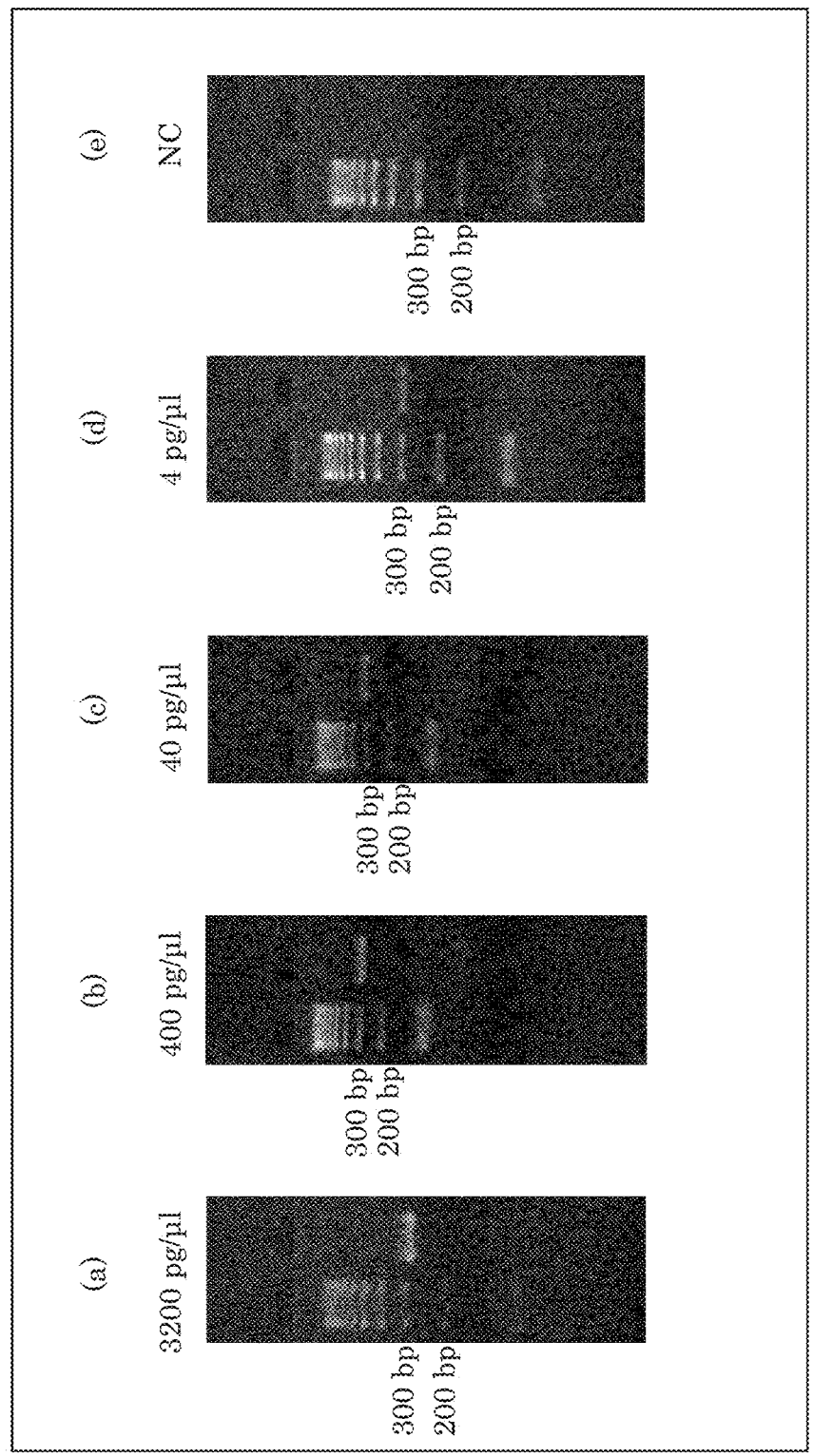
FIG. 9 is a diagram of images of gel electrophoresis showing standard DNA markers before and after the amplification with respect to the initial concentrations of human genome DNA, when human genome DNA is amplified using a nucleic acid amplification device according to an embodiment.

Moreover, FIG. 9 is a diagram of images of gel electrophoresis showing standard DNA markers before and after the amplification with respect to the initial concentrations of human genome DNA shown in FIG. 8. In FIG. 9, (a), (b), (c), (d), and (e) are images of the amplified products in the cases where the final concentrations of the human genome DNA were 3200 pg/μl, 400 pg/μl, 40 pg/μl, 4 pg/μl, and 0 pg/μl (NC), respectively.

As can be seen in FIG. 9, an increase in the amount of fluorescence representing the DNA amplification was observed and the human genome DNA was amplified to a desired amount, for each of the initial concentrations except for the NC.

Figure 10:
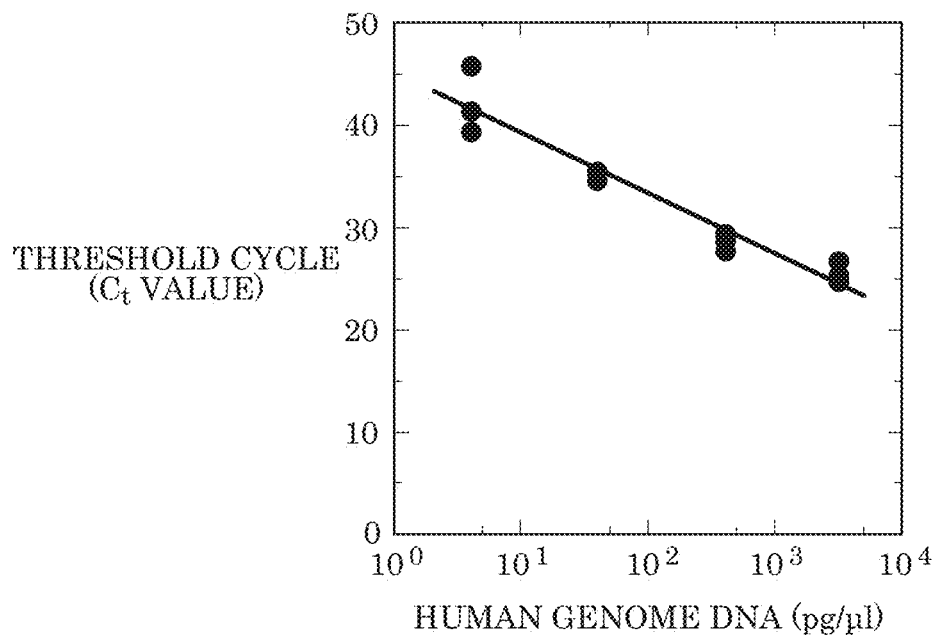
FIG. 10 is a diagram showing a relationship between the concentration of a reaction sample (human genome DNA) and a threshold cycle, when the human genome DNA is amplified using a nucleic acid amplification device according to an embodiment.

Moreover, FIG. 10 is a diagram showing a relationship between the concentration of the reaction sample (human genome DNA) shown in FIG. 8 and a threshold cycle.

As shown in FIG. 8, the cycle at the start of PCR varies depending on the initial concentration of the human genome DNA. Here, assume that a cycle equivalent to, for example, about 10% of a maximum value (saturation value) is defined as a threshold cycle (Ct value). With this, a significantly linear calibration curve can be obtained, as shown in FIG. 10. Using this calibration curve, an initial concentration of the human genome DNA can be quantitated.

(Example 2)

Next, Example 2 that is an example to detect *E. coli* genome DNA is described with reference to FIG. 11, FIG. 12, and FIG. 13.

Figure 11:
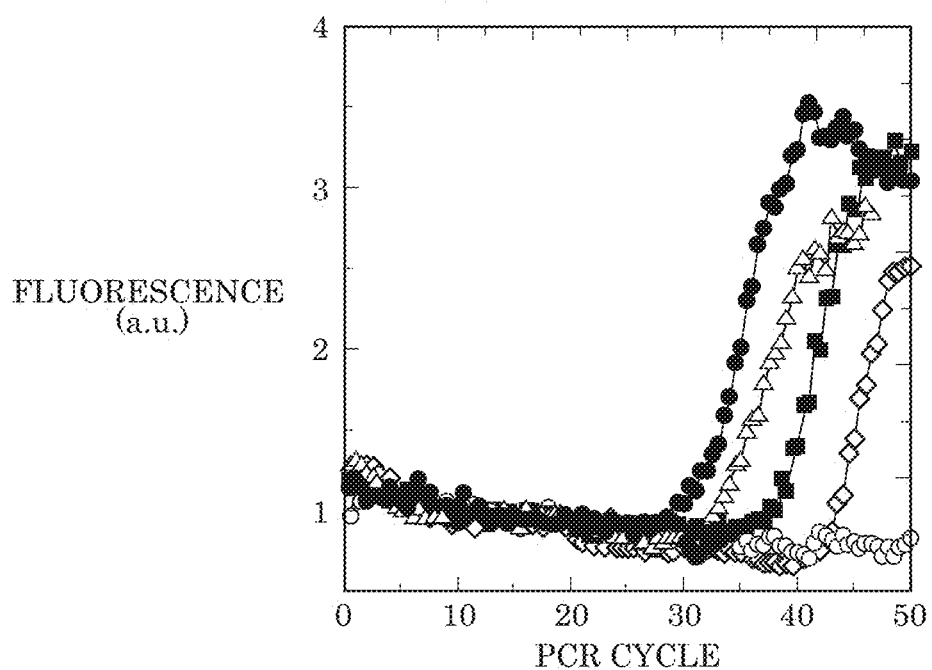
FIG. 11 is a diagram showing a relationship between a PCR cycle of a reaction solution and the amount of fluorescence (the amount of amplification) when *Escherichia coli* (*E. coli*) genome DNA is amplified using a nucleic acid amplification device according to an embodiment.

FIG. 11 is a diagram showing a relationship between a PCR cycle of the reaction solution and the amount of fluorescence (the amount of amplification) when *E. coli* genome DNA is amplified using the nucleic acid amplification device according to the embodiment. In FIG. 11, measurement results of optical detection performed using the nucleic acid amplification apparatus shown in FIG. 5 are shown.

In this experiment, a SpeedSTAR HS DNA Polymerase kit manufactured by TAKARA BIO INC. was used as a polymerase enzyme of the reaction sample (PCR reagent). This kit includes, in addition to the polymerase enzyme, a buffer solution and deoxynucleotide mix (dNTP Mix) necessary for reaction. To be more specific, 10× Fast buffer I, 0.2 mM of dNTP Mix, and 0.15 U/μl of SpeedSTAR HS DNA Polymerase included in this kit were used. Moreover, the following were added: 1 pg/μl of bovine serum albumin (BSA); 300 nM of forward primer (5'-CGGAAGCAACGCGTAAACTC-3'); 300 nM of reverse primer (5'-TGAGCGTCGCAGAACATTACA-3'); and 300 nM of a TaqMan probe (5'-FAM-CGCGTCCGATCACCTGCGTC-BHQ1-3'). It should be noted that this primer set targets uidA gene of *E. coli* and is disclosed in Reference Literature 1 (S. S. Silkie, M. P. Tolcher, K. L. Nelson, J. Microbiol. Method., vol. 72, pp. 275-281 (2008)). Also note that these are only examples and that other reagents having the same functions may be used.

Moreover, amplification characteristics were evaluated for each of the cases in which the respective final concentrations of the *E. coli* genome DNA were 1.9 pg/μl, 0.19 pg/μl, 0.019 pg/μl, and 0.0019 pg/μl. Furthermore, as a negative control (NC), amplification characteristics were also evaluated for the solution that did not contain *E. coli* genome DNA (0 pg/μl as the concentration of *E. coli* genome DNA).

As can be seen in FIG. 11, the amount of fluorescence increased with an increase in the number of PCR cycles in all the cases of the *E. coli* genome DNA concentrations. In other words, it can be seen that the amount of nucleic acid increased in all the cases.

Figure 12:
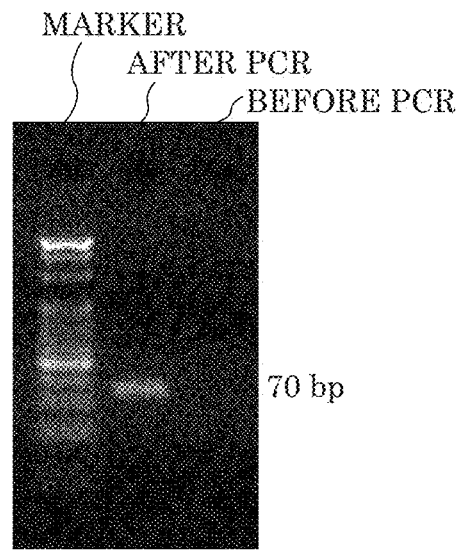
FIG. 12 is a diagram of an image of gel electrophoresis showing standard DNA markers before and after the amplification with respect to the initial concentration of *E. coli* genome DNA, when the *E. coli* genome DNA is amplified using a nucleic acid amplification device according to an embodiment.

Moreover, FIG. 12 is a diagram of an image of gel electrophoresis showing standard DNA markers before and after the amplification with respect to the initial concentration of the *E. coli* genome DNA shown in FIG. 11. In FIG. 12, the diagram shows, as a representative, the electrophoresis image of the amplified product of the *E. coli* genome DNA with the final concentration of 0.19 pg/μl.

As can be seen, an increase in the amount of fluorescence representing the DNA amplification was observed and the *E. coli* genome DNA was amplified to a desired amount, for each of the initial concentrations except for the NC. Moreover, the amplified product was observed at 70 bp, which was a desired DNA length.

Figure 13:
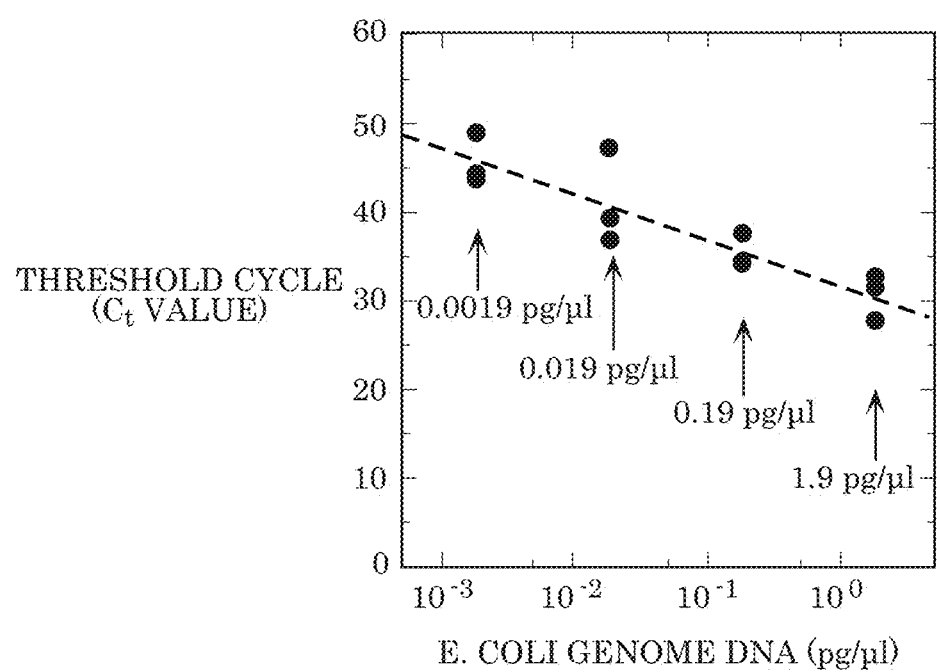
FIG. 13 is a diagram showing a relationship between the concentration of a reaction sample (*E. coli* genome DNA) and a threshold cycle, when the *E. coli* genome DNA is amplified using a nucleic acid amplification device according to an embodiment.

Moreover, FIG. 13 is a diagram showing a relationship between the concentration of the reaction sample (*E. coli* genome DNA) shown in FIG. 11 and a threshold cycle at startup.

As shown in FIG. 11, the cycle at the start of PCR varies depending on the initial concentration of the *E. coli* genome DNA. Here, assume that the fluorescence value before amplification is 1 and that a cycle having the amount of increased fluorescence of, for example, about 10% is defined as a threshold cycle (Ct value). With this, a significantly linear calibration curve can be obtained, as shown in FIG. 13. Using this calibration curve, an initial concentration of the *E. coli* genome DNA can be quantitated.

(Example 3)

Next, Example 3 that is an example to detect enterohemorrhagic *E. coli* O157 genome DNA is described with reference to FIG. 14, FIG. 15, and FIG. 16.

Figure 14:
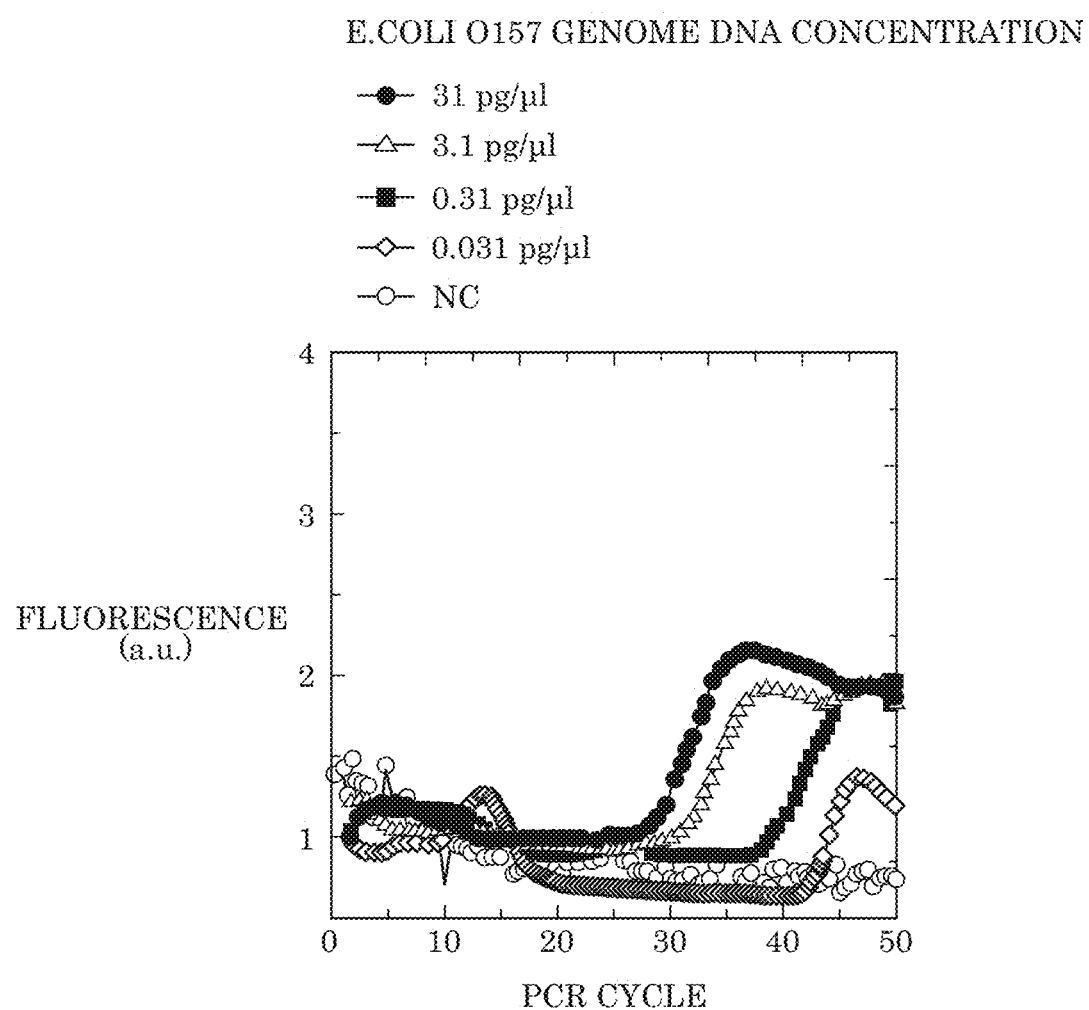
FIG. 14 is a diagram showing a relationship between a PCR cycle of a reaction solution and the amount of fluorescence (the amount of amplification) when enterohemorrhagic *E. coli* O157 genome DNA is amplified using a nucleic acid amplification device according to an embodiment.

FIG. 14 is a diagram showing a relationship between a PCR cycle of a reaction solution and the amount of fluorescence (the amount of amplification) when enterohemorrhagic *E. coli* O157 genome DNA is amplified using the nucleic acid amplification device according to the embodiment. In FIG. 14, measurement results of optical detection performed using the nucleic acid amplification apparatus shown in FIG. 5 are shown.

In this experiment, a SpeedSTAR HS DNA Polymerase kit manufactured by TAKARA BIO INC. was used as a polymerase enzyme of the reaction sample (PCR reagent). This kit includes, in addition to the polymerase enzyme, a buffer solution and deoxynucleotide mix (dNTP Mix) necessary for reaction. To be more specific, 10× Fast buffer I, 0.2 mM of dNTP Mix, and 0.15 U/µl of SpeedSTAR HS DNA Polymerase were used. Moreover, the following were added: 1 pg/µl of bovine serum albumin (BSA); 300 nM of forward primer (5'-CAATTTTCAGGGAATAACATTG-3'); 300 nM of reverse primer (5'-AAAGTTCAGATCTTGATGACATTG-3'); and 300 nM of a TaqMan probe (5'-FAM-TCAAGAGTTGCCCATCCTGCAGCAA-BHQ1-3'). It should be noted that this primer set targets eaeA gene of enterohemorrhagic *E. coli* O157 and is disclosed in Reference Literature 2 (D. R. Call, F. J. Brockman, D. P. Chandler, Int. J. Food Microbiol., vol. 67, pp. 71-80 (2001)). Also note that these are only examples and that other reagents having the same functions may be used.

Moreover, amplification characteristics were evaluated for each of the cases in which the respective final concentrations of the enterohemorrhagic *E. coli* O157 genome DNA were 31 pg/µl, 3.1 pg/µl, 0.31 pg/µl, and 0.031 pg/µl. Furthermore, as a negative control (NC), amplification characteristics were also evaluated for the solution that did not contain enterohemorrhagic *E. coli* O157 genome DNA (0 pg/µl as the concentration of enterohemorrhagic *E. coli* O157 genome DNA).

As can be seen in FIG. 14, the amount of fluorescence increased with an increase in the number of PCR cycles in all the cases of the enterohemorrhagic *E. coli* O157 genome DNA concentrations. In other words, it can be seen that the amount of nucleic acid increased in all the cases.

Figure 15:
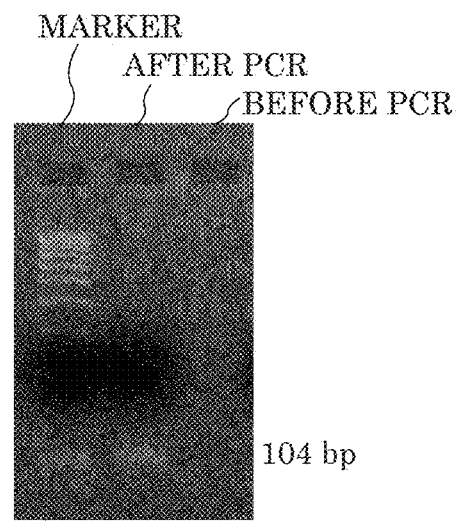
FIG. 15 is a diagram of an image of gel electrophoresis showing standard DNA markers before and after the amplification with respect to the initial concentration of enterohemorrhagic *E. coli* O157 genome DNA, when the enterohemorrhagic *E. coli* O157 genome DNA is amplified using a nucleic acid amplification device according to an embodiment.

Moreover, FIG. 15 is a diagram of an image of gel electrophoresis showing standard DNA markers before and after the amplification with respect to the initial concentration of the enterohemorrhagic *E. coli* O157 genome DNA shown in FIG. 14. In FIG. 15, the diagram shows, as a representative, the electrophoresis image of the amplified product of the enterohemorrhagic *E. coli* O157 genome DNA with the final concentration of 0.31 pg/µl.

As can be seen, an increase in the amount of fluorescence representing the DNA amplification was observed and the enterohemorrhagic *E. coli* O157 genome DNA was amplified to a desired amount, for each of the initial concentrations except for the NC.

Figure 16:
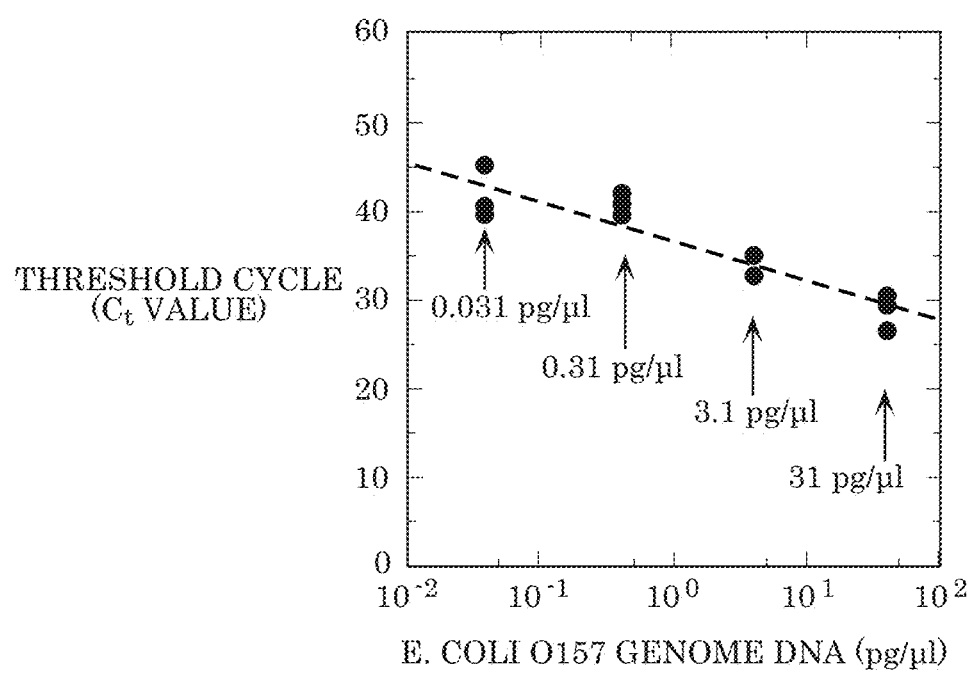
FIG. 16 is a diagram showing a relationship between the concentration of a reaction sample (enterohemorrhagic *E. coli* O157 genome DNA) and a threshold cycle, when the enterohemorrhagic *E. coli* O157 genome DNA is amplified using a nucleic acid amplification device according to an embodiment.

Moreover, FIG. 16 is a diagram showing a relationship between the concentration of the reaction sample (enterohemorrhagic *E. coli* O157 genome DNA) shown in FIG. 14 and a threshold cycle at startup.

As shown in FIG. 14, the cycle at the start of PCR varies depending on the initial concentration of the enterohemorrhagic *E. coli* O157 genome DNA. Here, assume that the fluorescence value before amplification is 1 and that a cycle having the amount of increased fluorescence of, for example, about 10% is defined as a threshold cycle (Ct value). With this, a significantly linear calibration curve can be obtained, as shown in FIG. 16. Using this calibration curve, an initial concentration of the enterohemorrhagic *E. coli* O157 genome DNA can be quantitated.

(Example 4)

Next, Example 4 that is an example to detect human IgA, which is protein, is described.

Protein contains no nucleic acid and thus cannot be amplified directly. For this reason, it is required to form a reaction system shown in FIG. 17, and eventually recover, amplify, and detect tag nucleic acid. The reaction concept is as follows.

Figure 17:
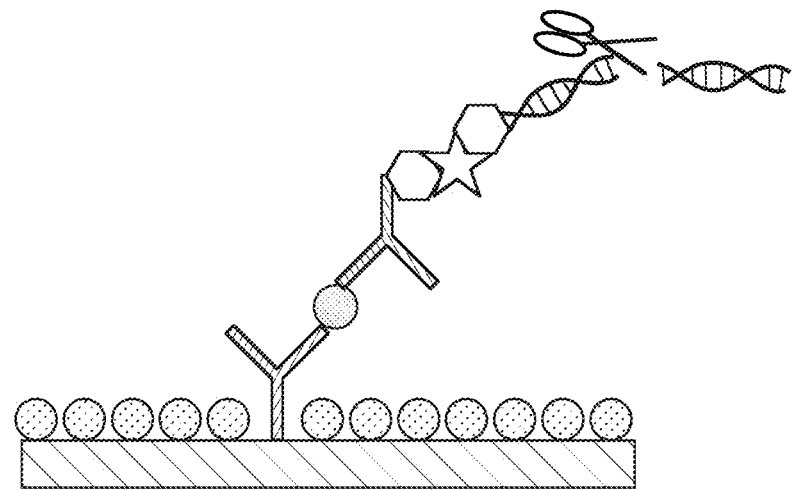
FIG. 17 is a diagram showing a procedure for explaining a reaction concept that is previously formed to detect human immunoglobulin A (IgA), which is protein.

Firstly, anti-human IgA antibody is fixed on a substrate. Then, human IgA antigen, which is a measuring object, is caused to react with anti-human IgA antibody, which is a secondary antibody. As a result, a sandwich structure is formed in which these two antibodies sandwich the antigen, as shown in FIG. 17. This sandwich structure is formed only when human IgA is present. With biotin modification on the secondary antibody, the secondary antibody can be easily caused to react with streptavidin. On top of this, a biotin-modified nucleic acid tag is caused to react with this. As a result, the reaction between biotin and streptavidin causes the nucleic acid tag to be captured into this complex. Lastly, using restriction enzyme, the nucleic acid is cleaved at a desired position. With this, the nucleic acid tag is separated for recovery, which thus enables PCR amplification.

It should be noted that the number of nucleic acid tags to be recovered from this reaction system is proportional to the concentration of antigen. Also note that amplification is possible in units of several nucleic acids in the subsequent PCR. Thus, using this reaction system, protein detection can be achieved with high sensitivity.

Figure 18:
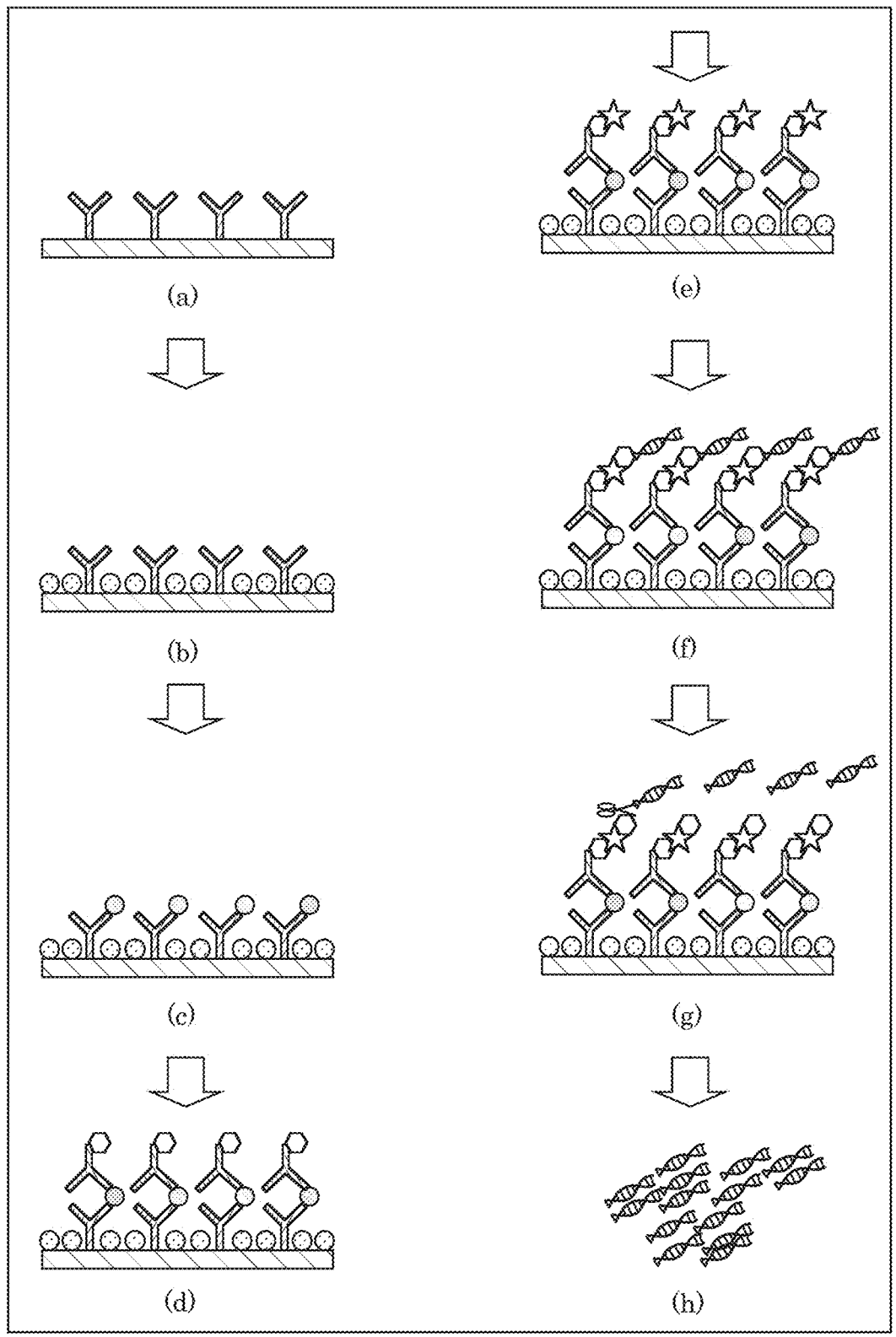
FIG. 18 is a diagram showing an example of the procedure to form a reaction system in FIG. 17.

Next, a specific experimental procedure to achieve the aforementioned reaction system is described with reference to FIG. 18. FIG. 18 is a diagram showing an example of the procedure to form the reaction system shown in FIG. 17.

Firstly, anti-human IgA antibody was added to phosphate buffered saline (PBS) so that the concentration was 0.01 mg/ml. Then, 50 µl of this was added to a plastic well and incubated for one hour at room temperature. As a result, anti-human IgA antibodies are fixed to the plastic well as shown in (a) of FIG. 18.

After the incubation, the aforementioned well was washed five times with PBS containing 0.05 wt % of polyoxyethylene (20) sorbitan monolaurate (Tween 20) (hereinafter, referred to as "PBST"). After this, 100 µl of BSA of 1 wt % (in PBS) was added to the washed well and incubated for 30 minutes at room temperature. As a result, BSA was caused to be absorbed onto the well's exposed surface where no anti-human IgA antibody was fixed, as shown in (b) of FIG. 18. This can be used for blocking the subsequent antigen from absorbing to the surface of the well in a non-specific manner. After the incubation, washing was performed again five times with PBST.

Next, human IgA protein, which was a measuring object, was adjusted to be $10^4$ ng/ml, $10^3$ ng/ml, $10^2$ ng/ml, $10^1$ ng/ml, and 0 ng/ml (in PBS). Then, 50 µl of each were added to different wells and incubated for one hour at room temperature ((c) in FIG. 18).

After the incubation, washing was performed five times with PBST. Then, 50 µl of 13 ng/ml of biotin-modified anti-human IgA antibody (in PBS) was added to each ((d) in FIG. 18).

After one hour of incubation at room temperature, washing was performed five times with PBST. Then, 50 µl of 0.1 pg/ml of streptavidin was added and incubated for 30 minutes at room temperature ((e) in FIG. 18).

After five times of washing with PBST, 50 µl of biotin-modified nucleic acid tag adjusted to be 5 pg/ml (in PBS) was added and incubated for 30 minutes at room temperature ((f) in FIG. 18).

After washing five times with PBST and three times with PBS, restriction enzyme was added. As the restriction enzyme, SspI sold by TAKARA BIO INC. was used. Using 10× buffer included in this kit, SspI was adjusted so that the final concentration was 2 U/μl. After this, 50 μl of this was added. With one hour of incubation at 37° C., the nucleic acid tag was separated from the antigen-antibody complex ((g) of FIG. 18) and finally the solution was recovered. Using this recovered solution, PCR amplification was performed ((h) of FIG. 18).

In the present experimental example, human IgA protein and anti-human IgA antibody were obtained from Bethyl Laboratories, Inc.

However, this reaction system can be changed as appropriate in accordance with a measuring object. Moreover, the nucleic acid tag was made by the following method.

To be more specific, using biotin-modified forward primer (5'-Biotin-GTGACAAAAAAACCACCCAAGC-3') and reverse primer (5'-TGAGCGTCGCAGAACATTACA-3') that target uidA gene of *E. coli*, PCR was performed using the *E. coli* genome as an amplification template. Then, by purification of the amplified product, the nucleic acid tag was made. It should be noted that the nucleic acid tag is not limited to the present example and may be changed as appropriate.

Figure 19:
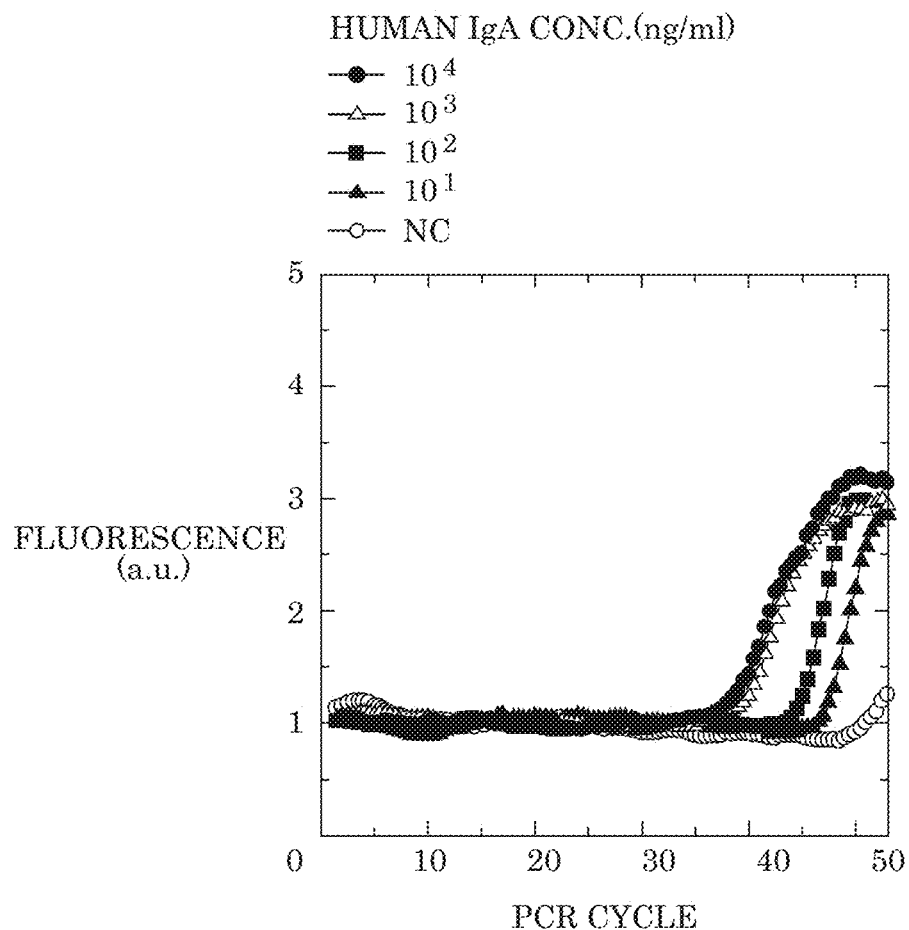
FIG. 19 is a diagram showing a relationship between a PCR cycle of a reaction solution and the amount of fluorescence (the amount of amplification) when a nucleic acid tag containing human IgA protein is amplified using a nucleic acid amplification device according to an embodiment.

FIG. 19 is a diagram showing a relationship between a PCR cycle of a reaction solution and the amount of fluorescence (the amount of amplification) when nucleic acid amplification is performed with the nucleic acid tag obtained in this way as the amplification template, using the nucleic acid amplification device according to the embodiment. In FIG. 19, measurement results of optical detection performed using the nucleic acid amplification apparatus shown in FIG. 5 are shown.

In this experiment, a SpeedSTAR HS DNA Polymerase kit manufactured by TAKARA BIO INC. was used as a polymerase enzyme of the reaction sample (PCR reagent). This kit includes, in addition to the polymerase enzyme, a buffer solution and deoxynucleotide mix (dNTP Mix) necessary for reaction. To be more specific, 10× Fast buffer I, 0.2 mM of dNTP Mix, and 0.15 U/μl of SpeedSTAR HS DNA Polymerase included in this kit were used. Moreover, the following were added: 1 pg/μl of bovine serum albumin (BSA); 300 nM of forward primer (5'-CG-GAAGCAACGCGTAAACTC-3'); 300 nM of reverse primer (5'-TGAGCGTCGCAGAACATTACA-3'); and 300 nM of a TaqMan probe (5'-FAM-CGCGTCCGATCACCT-GCGTC-BHQ1-3'). It should be noted that this primer set targets uidA gene of *E. coli* and is disclosed in Reference Literature 1 described above. Also note that these are only examples and that other reagents having the same functions may be used.

Moreover, amplification characteristics were evaluated for each of the cases in which the respective final concentrations of the human IgA protein were $10^4$ ng/ml, $10^3$ ng/ml, $10^2$ ng/ml, and $10^1$ ng/ml. Furthermore, as a negative control (NC), amplification characteristics were also evaluated for the solution that did not contain human IgA protein (0 pg/μl as the concentration of human IgA protein).

As can be seen in FIG. 19, the amount of fluorescence increased with an increase in the number of PCR cycles in all the cases of the human IgA protein concentrations. In other words, it can be seen that the amount of nucleic acid increased in all the cases.

Figure 20:
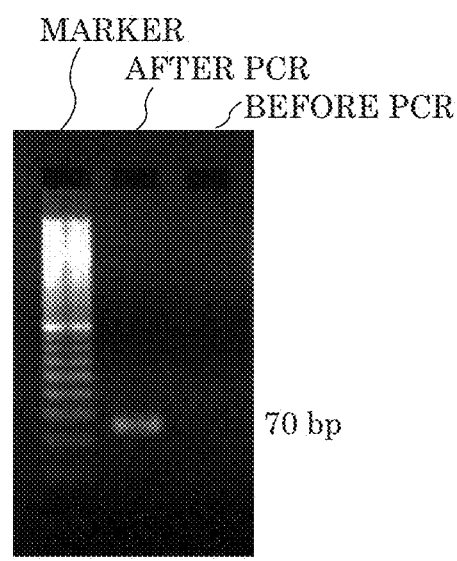
FIG. 20 is a diagram of an image of gel electrophoresis showing standard DNA markers before and after the amplification with respect to the initial concentration of human IgA protein, when human genome DNA is amplified using a nucleic acid amplification device according to an embodiment.

Moreover, FIG. 20 is a diagram of an image of gel electrophoresis showing standard DNA markers before and after the amplification with respect to the initial concentration of the human IgA protein shown in FIG. 19. In FIG. 20, the diagram shows, as a representative, the electrophoresis image of the amplified product of the human IgA protein with the final concentration of $10^2$ ng/ml.

As can be seen, an increase in the amount of fluorescence representing the DNA amplification was observed and the human IgA protein was amplified to a desired amount, for each of the initial concentrations. Although a slight amount of amplification can be seen in the case of 0 ng/ml, the amplification can be sufficiently distinct as compared to the case of $10^1$ ng/ml. Moreover, the amplified product was observed at 70 bp, which was a desired DNA length.

Figure 21:
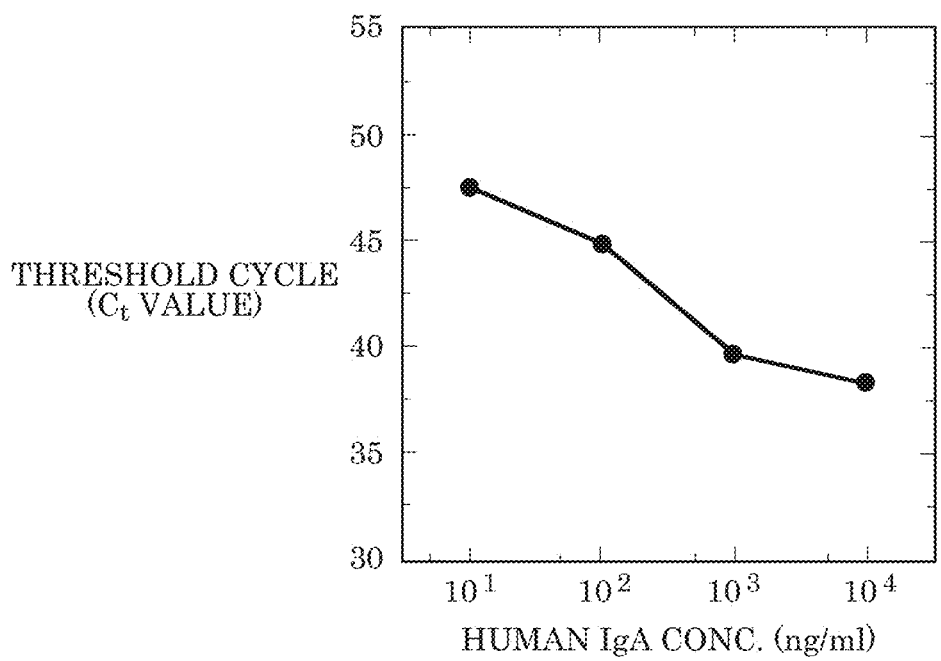
FIG. 21 is a diagram showing a relationship between the concentration of a reaction sample (human IgA protein) and a threshold cycle, when a nucleic acid tag containing the human IgA protein is amplified using a nucleic acid amplification device according to an embodiment.

Moreover, FIG. 21 is a diagram showing a relationship between the concentration of the reaction sample (human IgA protein) shown in FIG. 19 and a threshold cycle at startup.

As shown in FIG. 19, the cycle at the start of PCR varies depending on the initial concentration of the human IgA protein. Here, assume that the fluorescence value before amplification is 1 and that a cycle having the amount of increased fluorescence of, for example, about 10% is defined as a threshold cycle (Ct value). With this, a significantly linear calibration curve can be obtained, as shown in FIG. 21. Using this calibration curve, an initial concentration of the human IgA protein can be quantitated.

Figure 22:
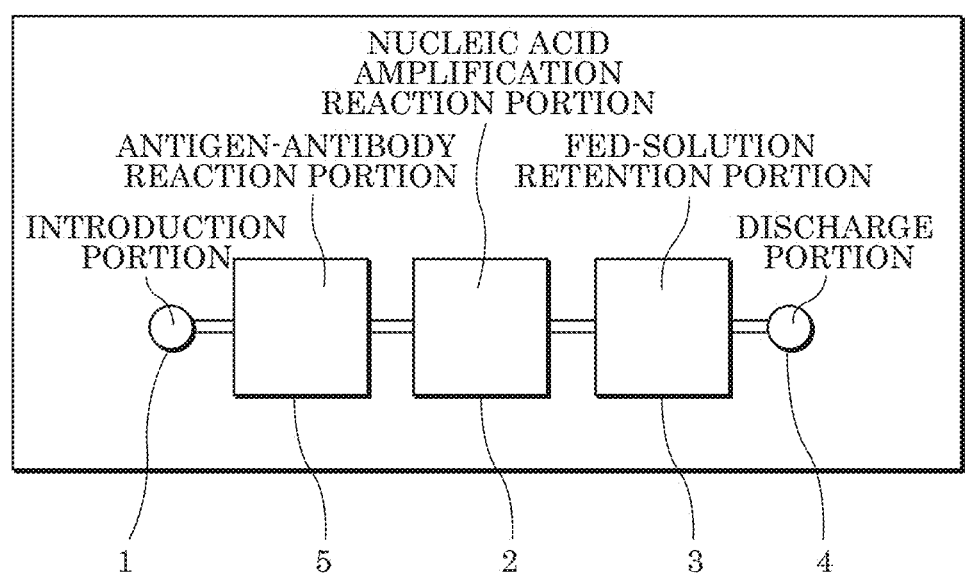
FIG. 22 is a diagram showing a schematic configuration of a nucleic acid amplification device according to first variation of the embodiment.

It should be noted that the reaction processes shown in (a) to (h) of FIG. 18 can be implemented on, for example, a nucleic acid amplification device shown in FIG. 22. The nucleic acid amplification device shown in FIG. 22 has a configuration in which antigen-antibody reaction portion 5 is additionally disposed between introduction portion 1 (sample introduction portion) and nucleic acid amplification reaction portion 2 in nucleic acid amplification device 100 shown in FIG. 1B.

Antibodies that specifically react to a measuring object substance are previously fixed to antigen-antibody reaction portion 5. The solution required for the procedure shown in FIG. 18 is delivered by drops from introduction portion 1 as needed, and is then fed to antigen-antibody reaction portion 5 for the reaction to proceed. Then, at the same time as the introduction of restriction enzyme in (g) of FIG. 18, the PCR reagent required for nucleic acid amplification is also introduced. With this, the PCR reagent can be fed to nucleic acid amplification reaction portion 2 together with the separated nucleic acid tag.

Figure 23:
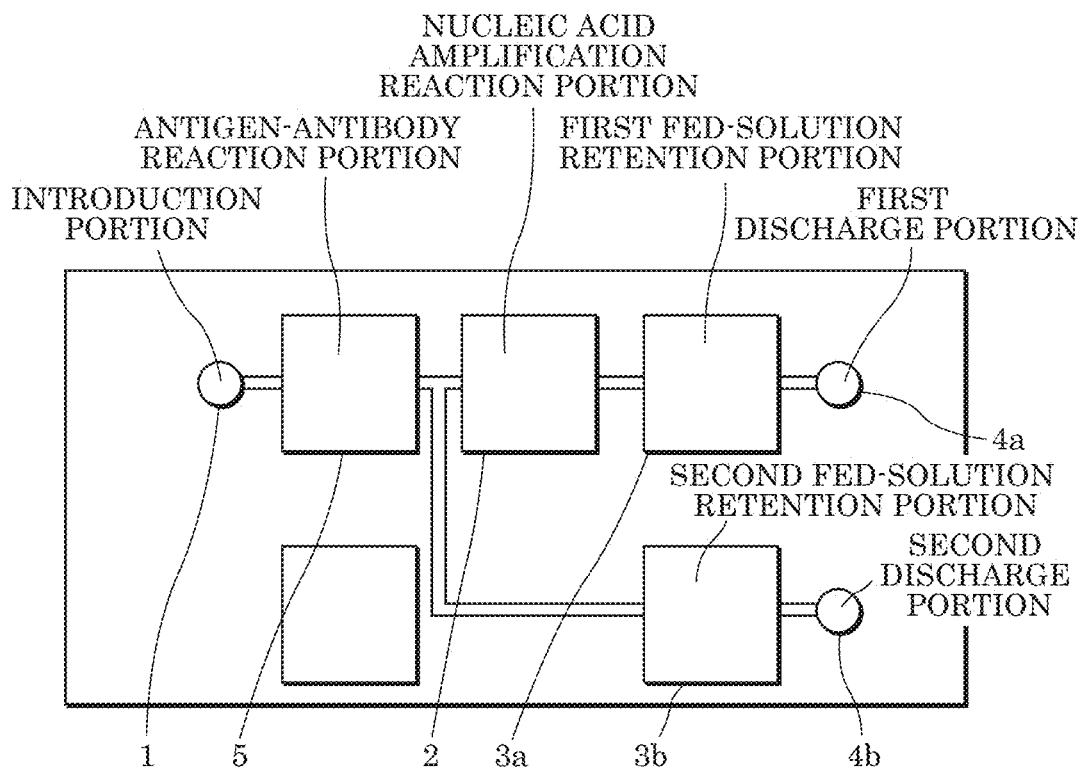
FIG. 23 is a diagram showing a schematic configuration of a nucleic acid amplification device according to second variation of the embodiment.

Moreover, FIG. 23 is a diagram showing a variation of the nucleic acid amplification device shown in FIG. 22. A nucleic acid amplification device shown in FIG. 23 has a configuration in which the flow channel branches off between antigen-antibody reaction portion 5 and nucleic acid amplification reaction portion 2. One of the two branched flow channels is connected to first discharge portion 4a via nucleic acid amplification reaction portion 2 and first fed-solution retention portion 3a. The other of the two branched flow channels is connected to second discharge portion 4b via second fed-solution retention portion 3b.

In this case, first discharge portion 4a is closed during the processes in (a) to (f) of FIG. 18. To close first discharge portion 4a, a seal may be placed on first discharge portion 4a, for example. Moreover, at the introduction of the restriction enzyme and PCR reagent in (g) of FIG. 18, second discharge portion 4b is closed at the same time as opening of first discharge portion 4a. Thus, the PCR reagent and nucleic acid tag are fed to nucleic acid amplification reaction portion 2 for PCR reaction to be executed.

With the configuration shown in FIG. 23, the solution feeding channel can be divided between antigen-antibody reaction and nucleic acid amplification reaction. This can prevent nucleic acid amplification reaction portion 2 from being polluted with unnecessary solution. Hence, the amount of nucleic acid amplification can be measured with high accuracy.

Figure 24:
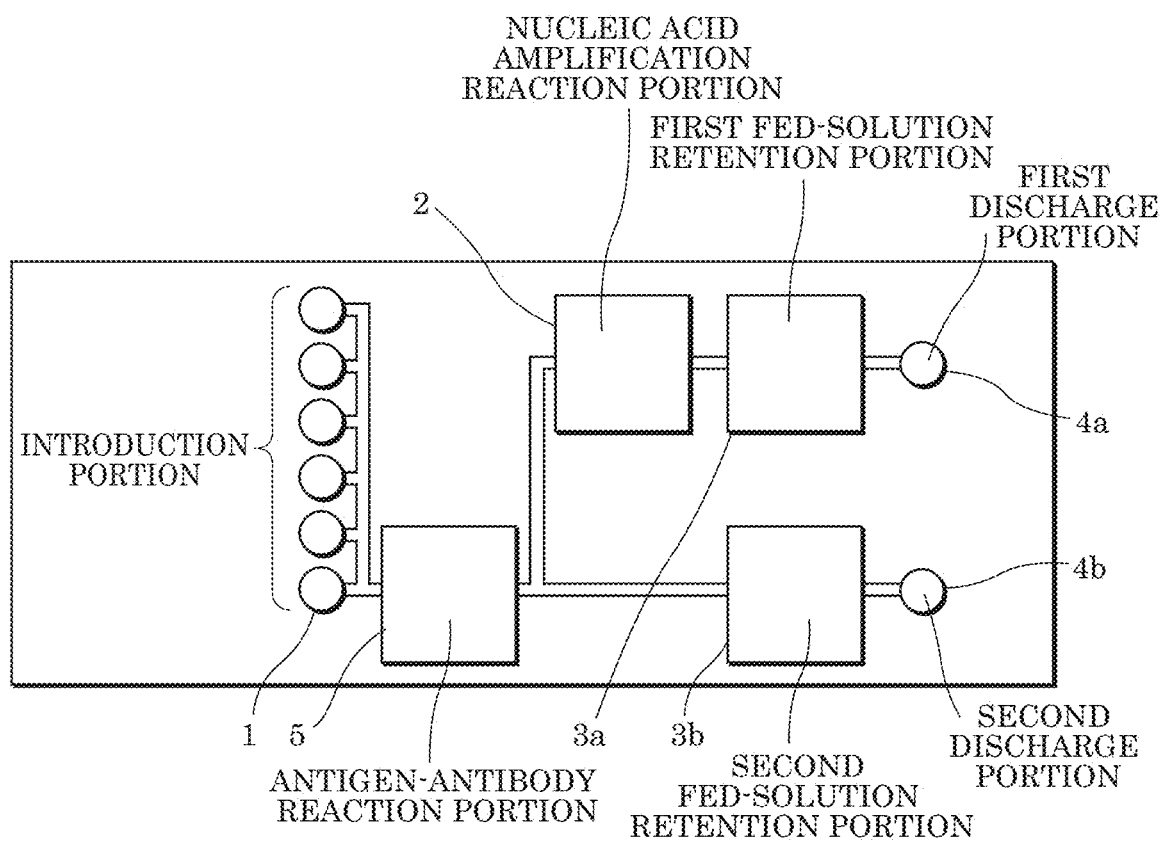
FIG. 24 is a diagram showing a schematic configuration of a nucleic acid amplification device according to third variation of the embodiment.

Moreover, FIG. 24 is a diagram showing an example with further variation made to the nucleic acid amplification device shown in FIG. 23. The nucleic acid amplification device shown in FIG. 24 includes at least two introduction portions 1. Thus, all the solutions required for the procedure shown in FIG. 18 can be separately introduced from respective introduction portions 1. For example, the reaction sample is sequentially introduced and fed from introduction portion 1 disposed close to antigen-antibody reaction portion 5.

With the configuration shown in FIG. 24, the reaction sample introduction can be completed at one time. This can enhance convenience for users.

CONCLUSION

With nucleic acid amplification device 100 according to the present embodiment described thus far, fed-solution retention portion 3 for retaining the reaction solution is disposed downstream of nucleic acid amplification reaction portion 2. To be more specific, the reaction solution fed from flow channel 110 (first flow channel 111) provided for nucleic acid amplification reaction portion 2 is retained in flow channel 110 (second flow channel 112) provided for fed-solution retention portion 3.

With this, the fluid front part with a low reaction efficiency out of the reaction solution can be withdrawn from nucleic acid amplification reaction portion 2. As a result, the target nucleic acid in the reaction solution can be amplified with high accuracy.

Moreover, in nucleic acid amplification device 100 according to the present embodiment, the reaction solution is fed through flow channel 110 by capillary force.

With this, the reaction solution can be fed easily without the use of an external pump, such as a syringe pump. Hence, the target nucleic acid can be amplified at low cost.

Furthermore, in nucleic acid amplification device 100 according to the present embodiment, nucleic acid amplification reaction portion 2 includes at least two temperature zones which have different temperatures. Flow channel 110 is formed to pass back and forth or cyclically through the at least two temperature zones.

With this, flow PCR can be achieved, and thus the nucleic acid can be amplified rapidly.

Moreover, in nucleic acid amplification device 100 according to the present embodiment, flow channel 110 (second flow channel 112) in fed-solution retention portion 3 includes a serpentine channel.

With this, second flow channel 112 can be formed to have a relatively large capacity even in a small space. On this account, the reaction solution can be retained in a compact space.

(Variations)

Hereinafter, variations of the nucleic acid amplification device according to the present invention are described. It should be noted that nucleic acid amplification devices described below have the same structure as nucleic acid amplification device 100 according to the above embodiment. Thus, in each of the variations, only the characteristic configurations are described.

(Variation 1)

Figure 25:
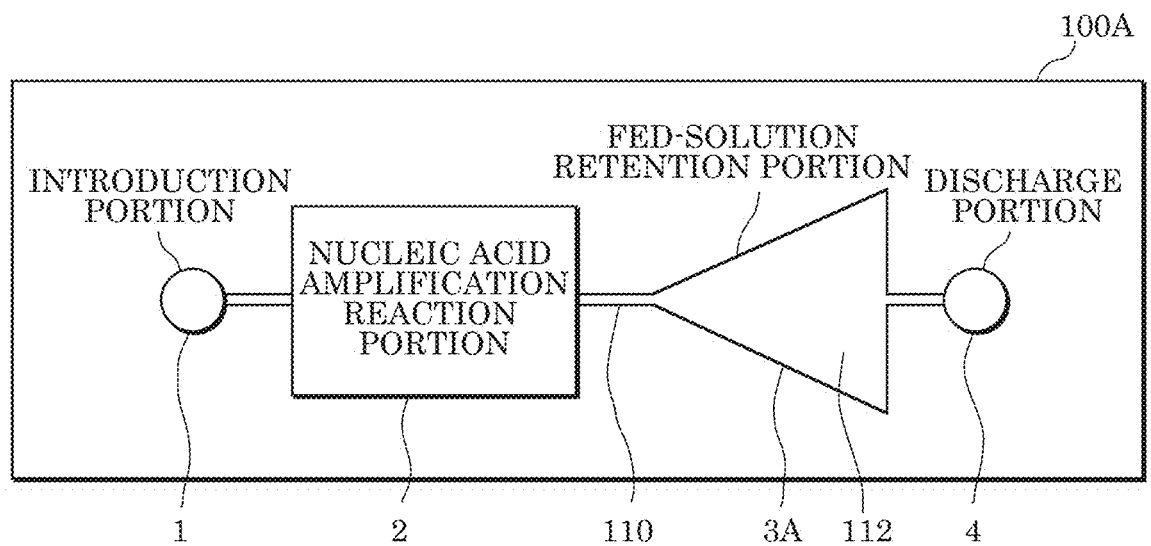
FIG. 25 is a diagram showing a schematic configuration of a nucleic acid amplification device according to Variation 1.

FIG. 25 is a diagram showing a schematic configuration of a nucleic acid amplification device according to Variation 1.

As shown in FIG. 25, in nucleic acid amplification device 100A according to the present variation, flow channel 110 (second flow channel 112) in fed-solution retention portion 3A includes an enlarged cross-sectional-area section (enlarged cross-sectional-area region) that gradually increases in cross-sectional area in the feeding direction of the reaction solution.

To be more specific, flow channel 110 (second flow channel 112) in the enlarged cross-sectional-area section of fed-solution retention portion 3A has a tapered shape that gradually increases in width in a direction from upstream to downstream. It should be noted that, in the present variation, flow channel 110 in the enlarged cross-sectional-area section of fed-solution retention portion 3A is constant in depth.

In this way, in nucleic acid amplification device 100A according to the present variation, the cross-sectional area of flow channel 110 (second flow channel 112) in fed-solution retention portion 3A gradually increases. With this, a large volume of reaction solution can be smoothly fed. Thus, the reaction solution can be retained in fed-solution retention portion 3A in a short time.

(Variation 2)

Figure 26:
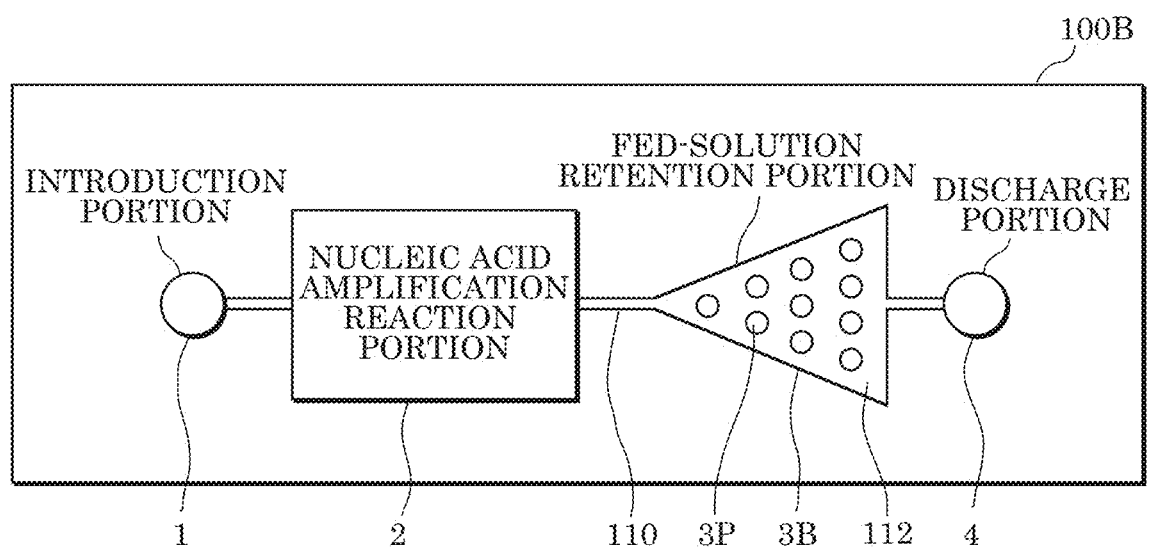
FIG. 26 is a diagram showing a schematic configuration of a nucleic acid amplification device according to Variation 2.

FIG. 26 is a diagram showing a schematic configuration of a nucleic acid amplification device according to Variation 2.

As shown in FIG. 26, fed-solution retention portion 3B in nucleic acid amplification device 100B according to the present variation includes an enlarged cross-sectional-area section, as is the case with fed-solution retention portion 3A according to Variation 1.

Furthermore, the enlarged cross-sectional-area section of fed-solution retention portion 3B (second flow channel 112) according to the present variation includes a plurality of pillars 3P. Each of pillars 3P is, for example, cylindrical in plan view, and is disposed upright in second flow channel 112.

In this way, in nucleic acid amplification device 100B according to the present variation, the enlarged cross-sectional-area section of fed-solution retention portion 3B (second flow channel 112) includes pillars 3P. With this, the feeding surface of the fluid front of the reaction solution can be made uniform in a plane. Since this can inhibit air bubbles from being caused in second flow channel 112, the feeding of the reaction solution can be stabilized.

In other words, when pillars as shown in FIG. 26 are not provided, part of the reaction solution that is closer to the hydrophilic wall surface of second flow channel 112 advances forward along the wall surface. This makes it easy for spaces (air bubbles) to be caused in the central portion of second flow channel 112. However, with pillars 3P, part of the reaction solution that is closer to the wall surface of second flow channel 112 can be inhibited from being fed ahead. Thus, the feeding surface of the fluid front of the reaction solution can be made uniform.

(Variation 3)

Figure 27:
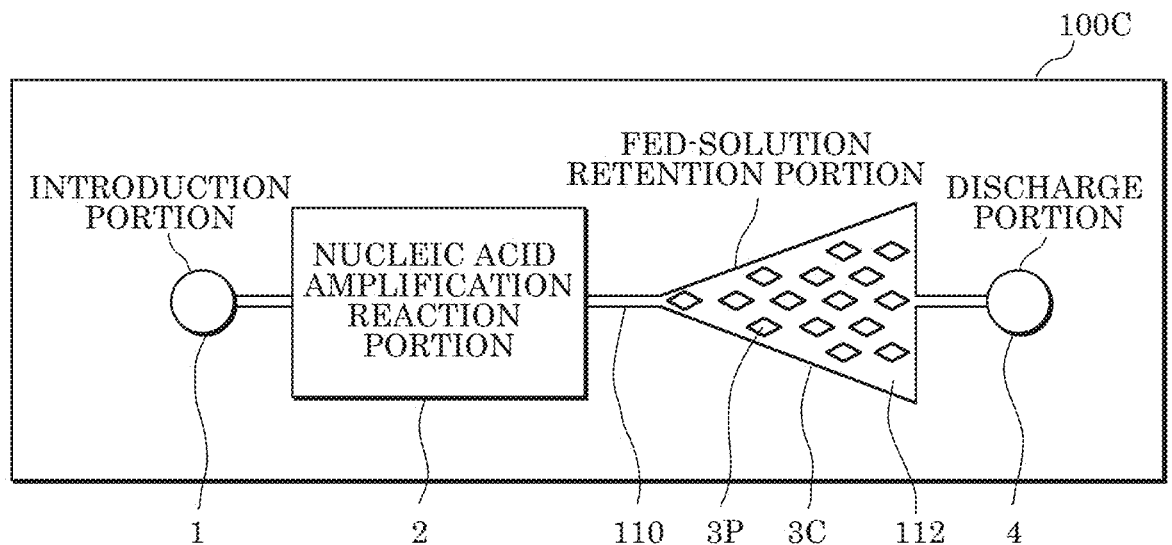
FIG. 27 is a diagram showing a schematic configuration of a nucleic acid amplification device according to Variation 3.

FIG. 27 is a diagram showing a schematic configuration of a nucleic acid amplification device according to Variation 3.

As shown in FIG. 27, fed-solution retention portion 3C in nucleic acid amplification device 100C according to the present variation includes an enlarged cross-sectional-area section, as is the case with fed-solution retention portion 3A according to Variation 1. In addition, fed-solution retention portion 3C also includes a plurality of pillars 3P.

Moreover, in the present variation, pillars 3P are regularly arranged. Each of pillars 3P is generally rhombic in plan view. With this, the feeding surface of the fluid front of the reaction solution can be made uniform.

It should be noted that the shape in plan view is not limited to generally rhombus, and that examples of the shape include a rhombus with rounded corners.

(Variation 4)

Figure 28:
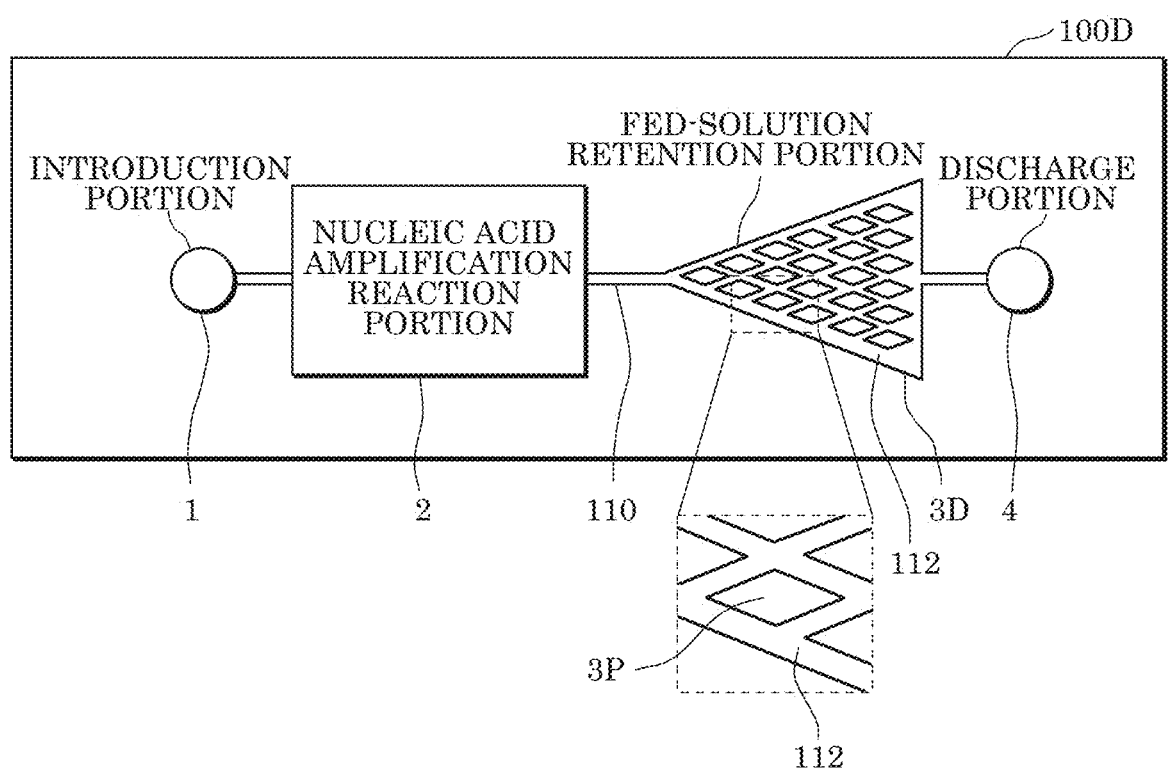
FIG. 28 is a diagram showing a schematic configuration of a nucleic acid amplification device according to Variation 4.

FIG. 28 is a diagram showing a schematic configuration of a nucleic acid amplification device according to Variation 4.

As shown in FIG. 28, fed-solution retention portion 3D in nucleic acid amplification device 100D according to the present variation includes an enlarged cross-sectional-area section and a plurality of pillars 3P that are generally rhombic in plan view, as is the case with fed-solution retention portion 3C according to Variation 3.

Furthermore, in the present variation, one side of each of pillars 3P is substantially parallel to a side wall of second flow channel 112 in the enlarged cross-sectional-area section of fed-solution retention portion 3D. With this, the feeding surface of the fluid front of the reaction solution can be made more uniform.

Moreover, in the present variation, pillars 3P are equally spaced from each other. With this, the feeding surface of the fluid front of the reaction solution can be made even more uniform.

(Variation 5)

Figure 29:
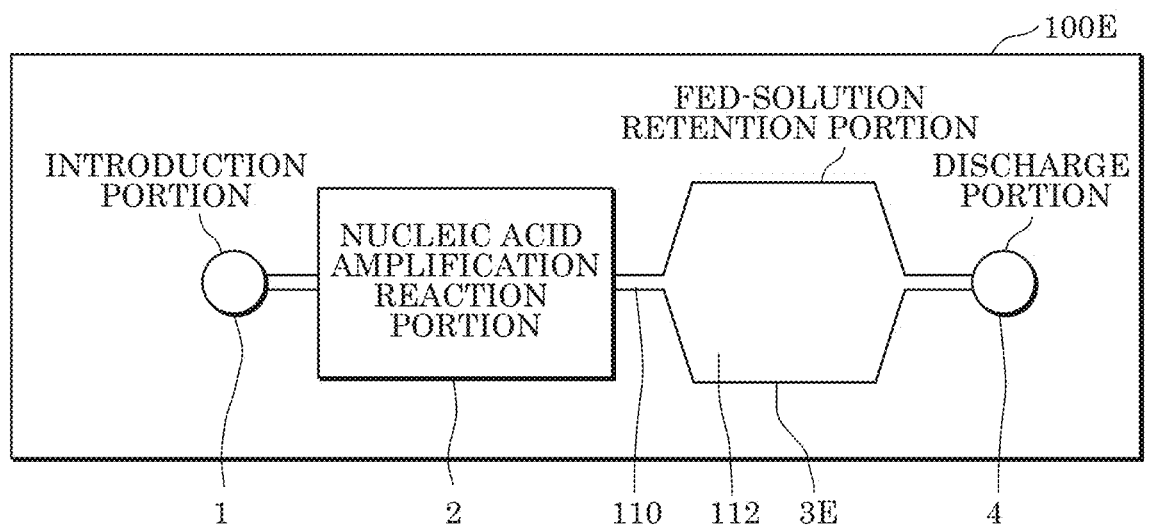
FIG. 29 is a diagram showing a schematic configuration of a nucleic acid amplification device according to Variation 5.

FIG. 29 is a diagram showing a schematic configuration of a nucleic acid amplification device according to Variation 5.

As shown in FIG. 29, in fed-solution retention portion 3E in nucleic acid amplification device 100E according to the present variation, second flow channel 112 has a cross-sectional area larger than the cross-sectional area of flow channel 110 (first flow channel) in nucleic acid amplification reaction portion 2. With this, a large volume of reaction solution can be retained in a compact space in fed-solution retention portion 3 (second flow channel).

(Variation 6)

Figure 30:
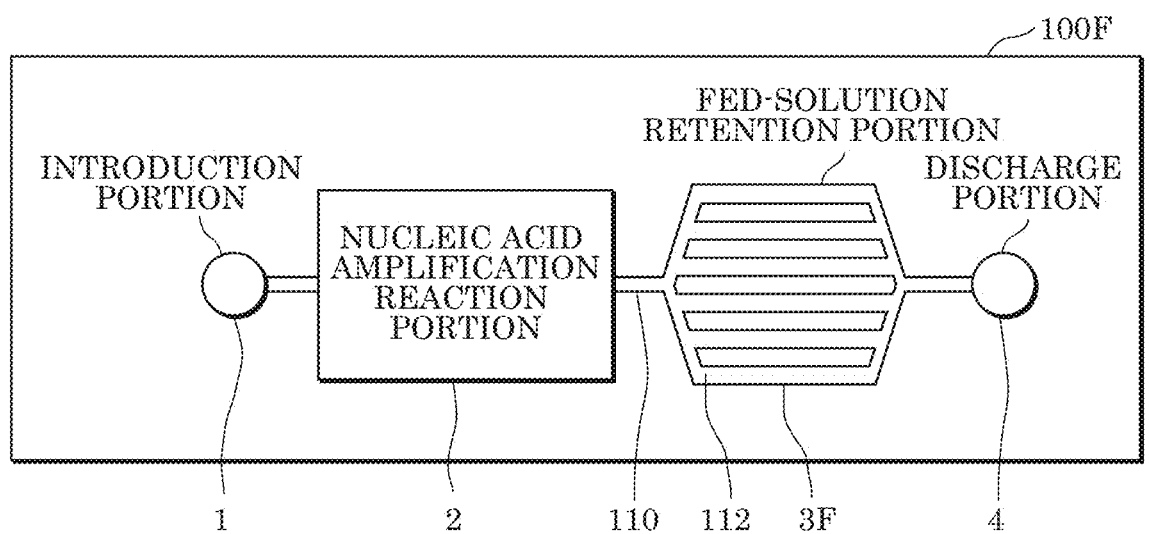
FIG. 30 is a diagram showing a schematic configuration of a nucleic acid amplification device according to Variation 6.

FIG. 30 is a diagram showing a schematic configuration of a nucleic acid amplification device according to Variation 6.

As shown in FIG. 30, in fed-solution retention portion 3F in nucleic acid amplification device 100F according to the present variation, second flow channel 112 has a portion that is divided into branches. It should be noted that although second flow channel 112 is divided into six branches in the present variation, this example is not intended to be limiting. For example, second flow channel 112 may be divided into two branches in a Y shape, or may be divided into a different number of branches.

In this way, with the branching of a portion of second flow channel 112 into a plurality of second flow channels 112, smooth connection with flow channel 110 can be achieved. In addition, a large volume of reaction solution can be retained in a compact space in fed-solution retention portion 3.

(Others)

Although the nucleic acid amplification device according to the present invention has been described on the basis of the above embodiment and variations, the present invention is not limited to the above embodiment and variations.

For example, in the above embodiment and variations, a flow PCR technique is used in which flow channel 110 in nucleic acid amplification reaction portion 2 is a serpentine channel and the reaction solution containing the target nucleic acid is repeatedly subjected to temperature changes. However, a PCR technique in which the reaction solution containing the target nucleic acid is repeatedly subjected to temperature changes may be used instead of the flow PCR technique. Here, it should be noted that, with the flow technique as in the above embodiment, PCR can be achieved more efficiently.

Moreover, although flow channel 110 is a serpentine channel in the above embodiment and variations, this example is not intended to be limiting. For example, a plurality of high temperature zones (95° C.) and a plurality of low temperature zones (60° C.) may be alternately arranged in lines. On this arrangement, a substrate on which a linear channel is formed may be disposed. With this, the flow channel may pass through the high temperature zone and the low temperature zone alternately.

Furthermore, heater 30 includes the two temperature zones in the above embodiment and variations. However, heater 30 may include three or more temperature zones having mutually different temperatures. In this case, the flow channel may be configured so that the reaction solution cyclically passes through these different temperature zones.

Moreover, the temperature setting for each of the temperature zones is performed using the corresponding heater block in the above embodiment and variations. However, a different temperature control component, such as a Peltier device, may be used for the temperature setting.

Other embodiments implemented through various changes and modifications conceived by a person of ordinary skill in the art based on the above embodiments and variations or through a combination of the structural components in the above embodiments unless such combination departs from the scope of the present invention may be included in the scope in an aspect or aspects according to the present invention.

REFERENCE MARKS IN THE DRAWINGS 2 nucleic acid amplification reaction portion
3, 3A, 3B, 3C, 3D, 3E, 3F fed-solution retention portion
3P pillar
100, 100A, 100B, 100C, 100D, 100E, 100F nucleic acid amplification device
110 flow channel
111 first flow channel
112 second flow channel
200 reaction solution

The invention claimed is:

1. A nucleic acid amplification device which includes a flow channel for feeding a reaction solution containing a target nucleic acid, the nucleic acid amplification device comprising:
 a nucleic acid amplification reaction portion that amplifies the target nucleic acid contained in the reaction solution; and
 a fed-solution retention portion that retains the reaction solution reacted in the nucleic acid amplification reaction portion,
 wherein the flow channel includes a first flow channel disposed in the nucleic acid amplification reaction portion and a second flow channel disposed in the fed-solution retention portion, the flow channel has a first end through which the reaction solution is introduced into the flow channel, and a second end through which the reaction solution is dischargeable from the flow channel, one end portion of the first flow channel and one end portion of the second flow channel are connected to the first end and the second end of the flow channel, respectively, and the other end portion of the first flow channel is connected to the other end portion of the second flow channel, the first end of the flow channel has an opening to the exterior of the amplification device for introduction of the reaction solution and the second end of the flow channel has an opening to the exterior of the amplification device, through which the reaction solution is dischargeable, a fluid front part of the reaction solution fed from the first flow channel flows into and is retained in the second flow channel, and wherein the second flow channel has a volumetric capacity that is 30% or more and less than 100% of a total volumetric capacity of the flow channel.

2. The nucleic acid amplification device according to claim 1,
wherein the reaction solution is fed through the flow channel by capillary force.

3. The nucleic acid amplification device according to claim 1,
wherein the flow channel has an inner surface that is a hydrophilic surface having a contact angle of less than 90°.

4. The nucleic acid amplification device according to claim 1,
wherein the nucleic acid amplification reaction portion includes at least two temperature zones which have different temperatures, and
the flow channel is structured to pass the reaction solution back and forth or cyclically through the at least two temperature zones.

5. The nucleic acid amplification device according to claim 1,
wherein the second flow channel includes a serpentine portion.

6. The nucleic acid amplification device according to claim 1,
wherein the second flow channel has a cross-sectional area larger than a cross-sectional area of the first flow channel.

7. The nucleic acid amplification device according to claim 1,
wherein the second flow channel has a portion that is divided into branches.

8. The nucleic acid amplification device according to claim 1,
wherein the second flow channel includes an enlarged cross-sectional-area section in which a cross-sectional area in a feeding direction of the reaction solution.

9. The nucleic acid amplification device according to claim 8,
wherein the enlarged cross-sectional-area gradually increases section of the second flow channel includes a plurality of pillars.

10. The nucleic acid amplification device according to claim 9,
wherein the plurality of pillars are regularly arranged, and each of the plurality of pillars is generally rhombic in plan view.

11. The nucleic acid amplification device according to claim 10,
wherein the enlarged cross-sectional-area section is structured such that the second flow channel gradually increases in width, and
one side of each of the plurality of pillars is substantially parallel to a side wall of the second flow channel in the enlarged cross-sectional-area section.

12. The nucleic acid amplification device according to claim 9,
wherein the plurality of pillars are equally spaced from each other.

* * * * *